(12) United States Patent
Ohiomoba

(10) Patent No.: US 11,605,464 B2
(45) Date of Patent: Mar. 14, 2023

(54) SYSTEMS AND METHODS FOR MACHINE LEARNING-BASED STATE PREDICTION AND VISUALIZATION

(71) Applicant: Marvin Behavioral Health Inc., San Marino, CA (US)

(72) Inventor: Patrick Ohiomoba, Boston, MA (US)

(73) Assignee: MARVIN BEHAVIORAL HEALTH INC., San Marino, CA (US)

( * ) Notice: Subject to any disclaimer, the term of this patent is extended or adjusted under 35 U.S.C. 154(b) by 0 days.

(21) Appl. No.: 17/661,530

(22) Filed: Apr. 29, 2022

(65) Prior Publication Data

US 2022/0350468 A1 Nov. 3, 2022

Related U.S. Application Data

(60) Provisional application No. 63/182,712, filed on Apr. 30, 2021, provisional application No. 63/267,385, filed on Jan. 31, 2022.

(51) Int. Cl.
*G16H 50/20* (2018.01)
*G16H 50/30* (2018.01)
*G06N 20/00* (2019.01)
*A61B 5/16* (2006.01)
(Continued)

(52) U.S. Cl.
CPC .............. *G16H 50/20* (2018.01); *A61B 5/165* (2013.01); *G06F 3/04842* (2013.01); *G06N 20/00* (2019.01); *G16H 50/30* (2018.01); *G16H 20/70* (2018.01)

(58) Field of Classification Search
CPC ........ G06F 3/04842; A61B 5/16; G06N 20/00
See application file for complete search history.

(56) References Cited

U.S. PATENT DOCUMENTS

| 8,700,012 B2 * | 4/2014 | Ferren .................. G06F 3/02 |
| | | 715/708 |
| 9,424,532 B1 | 8/2016 | Abedini et al. |
| 9,679,060 B2 * | 6/2017 | Hebenthal ........... G06F 16/9535 |

(Continued)

OTHER PUBLICATIONS

Dianxi Shi, Xi Chen, Jing Wei, Ruosong Yang; User Emotion Recognition Based on Multi-Class Sensors of Smartphone; 2015; IEEE Computer Society; pp. 478-485 (Year: 2015).*

(Continued)

*Primary Examiner* — Scott S Trotter
(74) *Attorney, Agent, or Firm* — Ahmann Kloke LLP

(57) ABSTRACT

Determining input data for at least one machine learning model based on electronic data of a user. Predicting, based on the input data and the at least one machine learning model, a mental state of the user, the mental state comprising mood values, uncertainty values, and magnitude values, each mood value being associated with a corresponding uncertainty value of the uncertainty values and a corresponding magnitude value of the magnitude values, the magnitude value indicating a relative strength or weakness of the associated mood value. Selecting and arranging, based on the predicted mental state, a subset of graphical elements, each graphical element being associated with a corresponding mood value of the set of mood values, and each graphical element of the subset of graphical elements being associated with the predicted mental state of the user.

17 Claims, 11 Drawing Sheets

(51) Int. Cl.
    *G06F 3/04842*     (2022.01)
    *G16H 20/70*     (2018.01)

(56) References Cited

U.S. PATENT DOCUMENTS

| | | | |
|---|---|---|---|
| 10,061,977 B1* | 8/2018 | Chang | G06V 40/175 |
| 10,628,528 B2* | 4/2020 | He | G06F 40/35 |
| 10,643,213 B1* | 5/2020 | Bermudez | G06Q 20/389 |
| 2009/0292713 A1* | 11/2009 | Jung | G06F 40/20 |
| 2010/0280579 A1 | 11/2010 | Denison et al. | |
| 2010/0305963 A1 | 12/2010 | Firminger et al. | |
| 2017/0262606 A1 | 9/2017 | Abdullah et al. | |
| 2020/0245949 A1 | 8/2020 | Dagum | |
| 2021/0104312 A1 | 4/2021 | Moskowitz | |
| 2021/0350917 A1 | 11/2021 | Curtis | |
| 2021/0406912 A1* | 12/2021 | Beilis | H04L 67/14 |

OTHER PUBLICATIONS

Clifton B. Parker, "Emotional fit important between a patient's desired feelings and physician, Stanford research shows" Stanford News, dated Apr. 2, 2015 and verified as having been available at least as far back as Jun. 11, 2016 on archive.org (Year: 2016).

* cited by examiner

Mapping a set of mood values, a set of uncertainty values, and a set of magnitude values to a coordinate system, the coordinate system comprising a plurality of different mood regions, wherein each of the set of mood values is mapped to the coordinate system as a corresponding user point in the coordinate system, and wherein each of the corresponding uncertainty values is mapped as a corresponding radius originating at the corresponding point in the coordinate system
402

Identifying at least a first mood region of the plurality of different mood regions that includes
at least one corresponding user mapped therein
404

Identifying at least a second mood region of the plurality of different mood regions that does not include any corresponding user points mapped therein, and includes at least a portion of a first radius of the corresponding radii mapped in the coordinate system
406

FIG. 4

SYSTEMS AND METHODS FOR MACHINE LEARNING-BASED STATE PREDICTION AND VISUALIZATION

CROSS-REFERENCE TO RELATED APPLICATIONS

The present application claims priority to U.S. Provisional Patent Application Ser. No. 63/182,712 filed Apr. 30, 2021, entitled "SYSTEMS AND METHODS FOR MACHINE LEARNING-BASED STATE PREDICTION AND VISUALIZATION," and U.S. Provisional Patent Application Ser. No. 63/267,385, filed on Jan. 31, 2022, entitled "SYSTEMS AND METHODS FOR MACHINE LEARNING-BASED PREDICTIVE MATCHING," both of which are hereby incorporated by reference herein.

TECHNICAL FIELD

This disclosure pertains to state prediction and visualization. More specifically, this disclosure pertains to machine learning-based state prediction and visualization.

BACKGROUND

Under conventional approaches, computing systems generically present graphical elements to a user. For example, a set of graphical elements may be presented for selection by a user as a generic list. However, since the graphical elements are presented generically, they are not typically presented efficiently for any given user. Accordingly, the computing system may have to select and present a relatively large number of graphical elements before a user selects an appropriate graphical element, if any is selected at all. This can be computationally inefficient (e.g., in terms of processing, memory, graphical display, and/or rendering) at least because it can require the computing system to process, store, render and/or display a relatively large number of different graphical elements, and consume a relatively large portion of a graphical display (e.g., a graphical user interface).

SUMMARY

Various embodiments of the present disclosure include systems, methods, and non-transitory computer readable media configured to obtain electronic data of a user. Input data is determined for at least one machine learning model based on the electronic data of the user. A mental state of the user is predicted based on the input data and the at least one machine learning model. The mental state comprises a set of mood values, a set of uncertainty values, and a set of a magnitude values. Each mood value of the set of mood values is associated with a corresponding uncertainty value of the set of uncertainty values and a corresponding magnitude value of the set of magnitude values. The magnitude values each indicate a relative strength or weakness of the associated mood value. A subset of graphical elements is selected and arranged, by the computing system based on the predicted mental state of the user, from a set of graphical elements. Each graphical element of the set of graphical elements is associated with a corresponding mood value of the set of mood values. Each graphical element of the subset of graphical elements is associated with the predicted mental state of the user. Presentation is facilitated, via a graphical user interface (GUI), of the subset of graphical elements according to the selection and arrangement of the subset of graphical elements. A user selection of a particular graphical element of the subset of graphical elements is received in response to the user interacting with the GUI presenting the subset of graphical elements according to the selection and arrangement of the subset of graphical elements. Presentation is facilitated, via the GUI in response to the user selection, of the user selected graphical element of the particular graphical element of the subset of graphical elements.

In some embodiments, each mood value of the set of mood values is associated with a corresponding point in time.

In some embodiments, the set of mood values comprise an angry mood value, a sad mood value, and a happy mood value.

In some embodiments, the electronic data includes text messages sent by the user, email messages sent by the user, voice data of the user, image data of the user, and one or more physical orientations of a device of a user.

In some embodiments, the systems, methods, and non-transitory computer readable media are further configured to perform mapping the set of mood values, the set of uncertainty values, and the set of magnitude values to a coordinate system, the coordinate system comprising a plurality of different mood regions, wherein each of the set of mood values is mapped to the coordinate system as a corresponding user point in the coordinate system, and wherein each of the corresponding uncertainty values is mapped as a corresponding radius originating at the corresponding point in the coordinate system; identifying at least a first mood region of the plurality of different mood regions that includes at least one corresponding user mapped therein; identifying at least a second mood region of the plurality of different mood regions that does not include any corresponding user points mapped therein, and includes at least a portion of a first radius of the corresponding radii mapped in the coordinate system; and wherein the mental state of the user is predicted based on the identified at least a first mood region of the plurality of different moods regions, the identified at least a second mood region of the plurality of different mood regions, and the magnitude values associated with the at least one corresponding user point mapped in the at least a first mood region of the plurality of different moods regions and the first radius of the corresponding radii mapped in the coordinate system.

In some embodiments, the coordinate system comprises a two-dimensional coordinate system.

In some embodiments, the coordinate system comprises a three-dimensional coordinate system.

In some embodiments, each mood value of the set of mood values is associated with a corresponding point in time.

In some embodiments, the set of graphical elements comprises a set of emojis.

These and other features of the systems, methods, and non-transitory computer readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

BRIEF DESCRIPTION OF THE DRAWINGS

FIG. 4 depicts a flowchart of an example of a method of mental state prediction according to some embodiments.

DETAILED DESCRIPTION

A claimed solution rooted in computer technology overcomes problems specifically arising in the realm of computer technology. In various embodiments, a computing system is configured to predict a mental state of a user based on machine learning, and facilitate presentation of one or more graphical elements (e.g., emojis) based on the predicted mental state. More specifically, the computing system may obtain electronic data of a user. For example, the computing system may scan a user's device (e.g., smartphone) and/or associated user accounts (e.g., social media accounts) to obtain data from text messages, email messages, social media services (e.g., Facebook), voice data, image data, and/or the like. The computing system may use a machine learning model to predict a mental state of the user based on the obtained electronic data. In some embodiments, a mental state may be generally defined as a distribution of mood values (or, simply, moods) over time. For example, mood values may include "angry," "sad," "happy," and/or other predefined or otherwise generally understood moods. Accordingly, it will be appreciated that, in some embodiments, a mood value is discrete, while a mental state is contiguous. The computing system, based on the predicted mental state, can intelligently select and/or arrange, and/or otherwise manipulate, graphical elements for presentation to a user (e.g., via a graphical user interface).

Accordingly, the computing system may provide a technological benefit over traditional systems which are typically limited to providing generic lists of graphical elements to different users. More specifically, the computing system can be computationally efficient (e.g., in terms of processing, memory, graphical display, and/or rendering) relative to traditional systems because it may not need to process, store, render and/or display a relatively large number of different graphical elements, and it may consume a relatively smaller portion of a graphical display (e.g., a graphical user interface). Furthermore, the computing system may reduce user interaction time with a device (e.g., thereby reducing battery usage, processor usage, etc.) by providing the user with more relevant graphical elements that a user may select without having to scroll through many different graphical elements.

Figure 1:
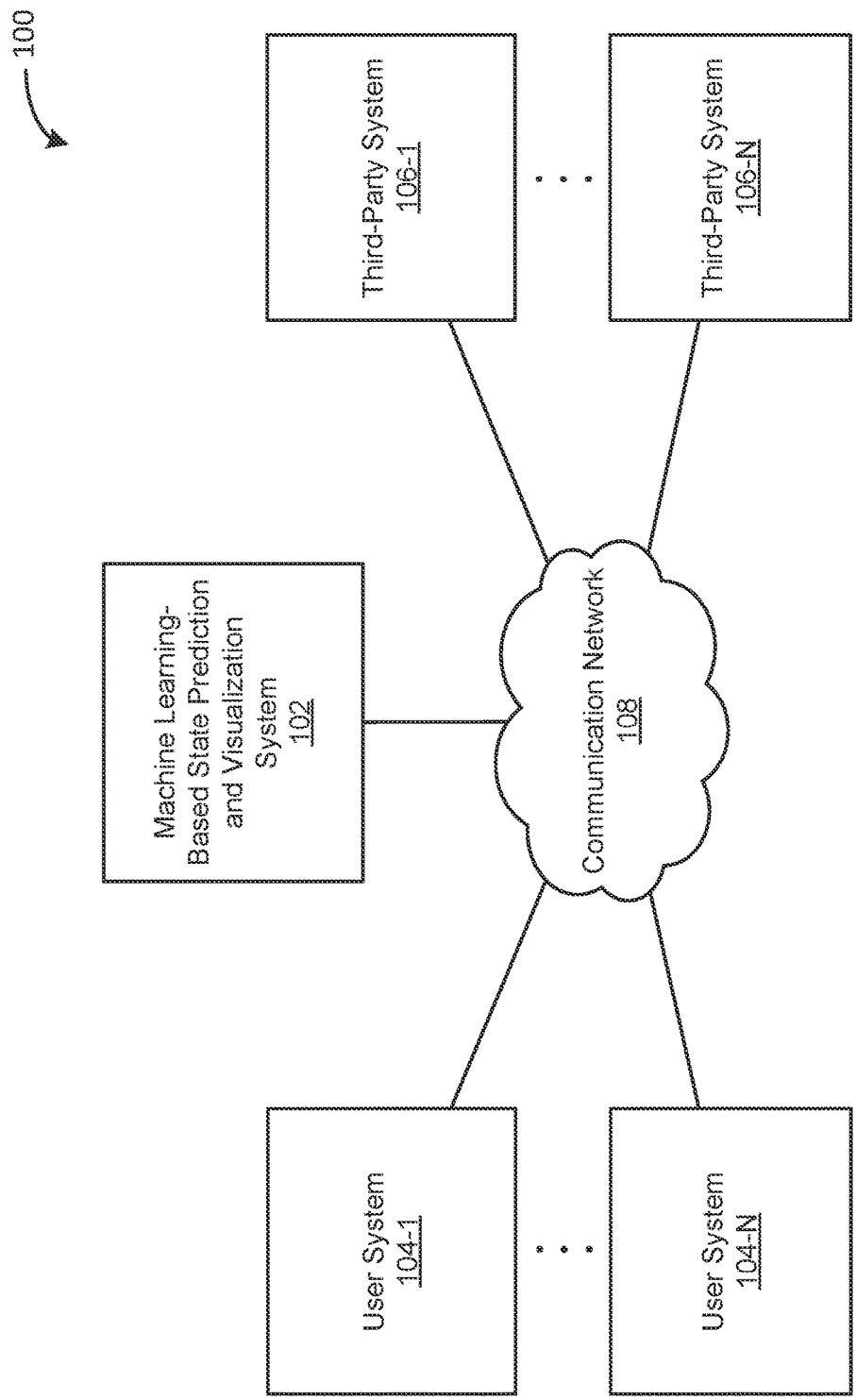
FIG. 1 depicts a diagram of an example system using machine learning to predict mental state and to select and arrange graphical elements based on the predicted mental state according to some embodiments.

FIG. 1 depicts a diagram of an example system 100 using machine learning to predict mental state and to select and arrange graphical elements based on the predicted mental state according to some embodiments. In some embodiments, graphical elements can be a type of emotional indicator, and the systems and methods described herein can operate on (e.g., select, arrange, manipulate, and/or the like), and otherwise utilize, emotional indicators in the same manner as graphical elements. Thus, for example, the system 100 may use machine learning to predict mental state and to select, arrange and/or otherwise manipulate emotional indicators based on the predicted mental state. Emotional indicators can include graphical elements (e.g., emojis), audio elements (e.g., voices), haptic elements, video elements, animation elements, and/or the like. Thus, in some embodiments, the systems and methods described herein can predict mental state as described in this paper in order to select, arrange, manage, manipulate, visualize, facilitate presentation, and/or perform any of the other functions described herein, for any type of emotional indicator in the same or similar manner as graphical elements. In the example of FIG. 1, the system 100 includes a machine learning-based state prediction and visualization system 102, user systems 104-1 to 104-N (individually, the user system 104, collectively, the user systems 104), third-party systems 106-1 to 106-N (individually, the third-party system 106, collectively, the third-party systems 106), and a communication network 108.

The machine learning-based state prediction and visualization system 102 may function to predict one or more mental states of a user (or set of users) based on machine learning. In some embodiments, the machine learning-based state prediction and visualization system 102 may function to select, arrange, manage, visualize, and/or otherwise manipulate and/or facilitate presentation of graphical elements (e.g., emojis), and/or other types of emotional indicators, based on the machine learning-predicted mental state of the user. In various embodiments, functionality of the machine learning-based state prediction and visualization system 102 may be performed by one or more servers (e.g., a cloud-based server) and/or other computing devices. The machine learning-based state prediction and visualization system 102 may be implemented by a cloud-computing platform.

In some embodiments, the machine learning-based state prediction and visualization system 102 may function to scan and/or other obtain electronic data from user systems (e.g., user systems 104, discussed below) and/or third-party systems (e.g., third-party systems 106, discussed below). For example, the machine learning-based state prediction and visualization system may scan text messages, email messages, voice data, image data, and/or the like. The machine learning-based state prediction and visualization system 102 may use some or all of this electronic data to provide input to a machine learning model that predicts a mental state of the user based on the input.

In some embodiments, the machine learning-based state prediction and visualization system may function to select, arrange, manage, visualize, and/or otherwise facilitate presentation of one or more graphical elements (e.g., emojis), and/or other types of emotional indicators, through a graphical user interface based on one or more predicted mental states. For example, the machine learning-based state prediction and visualization system may facilitate a mobile application executing on a user system to present a set of emojis associated with the predicted mental state, rather than merely presenting a general list of emojis or the most commonly used or most recently used emojis.

The user systems 104 may function to receive, transmit, and/or present (e.g., display) information. For the example, the user systems 104 may generate and/or present graphical user interfaces that a user may interact with. In various embodiments, functionality of the user systems 104 may be performed by one or more devices (e.g., smartphones, laptop computers, desktop computers, tablets, servers) and/or other computing devices.

In some embodiments, the user systems 104 may function to receive, transmit, obtain, and/or present electronic data of a user and/or associated with a user. For example, electronic data may include texts messages (e.g., SMS messages, iMessages, and/or the like), email messages, social media data (e.g., data from a user's social media account), voice data (e.g., audio recording a user speaking, a voicemail messages, a phone or video call, and/or the like), image data (e.g., a picture of user, a video of a user), haptic data (e.g., pressure from user's hand holding a device), physical location data (e.g., GPS data), physical orientation data (e.g., a physical orientation of device of user at the time other electronic data is captured or other time), and/or the like. In some embodiments, electronic data may include encrypted data (e.g., data from an encrypted text message communication) and/or decrypted data.

The third-party systems 106 may function to receive, transmit, and/or present information. For example, the third-party systems 106 may comprise social media systems (e.g., Facebook, Instagram, TikTok, LinkedIn, email systems, text messages systems, and/or the like). In some embodiments, functionality of the third-party systems 106 may be performed by one or more servers (e.g., cloud-based servers) and/or other computing devices.

The communications network 108 may represent one or more computer networks (e.g., LAN, WAN, or the like) or other transmission mediums. The communication network 108 may provide communication between systems 102-106 and/or other systems and/or components thereof (e.g., engines and/or datastores of the systems 102-106) described herein. In some embodiments, the communication network 108 includes one or more computing devices, routers, cables, buses, and/or other network topologies (e.g., mesh, and the like). In some embodiments, the communication network 108 may be wired and/or wireless. In various embodiments, the communication network 108 may include the Internet, one or more wide area networks (WANs) or local area networks (LANs), one or more networks that may be public, private, IP-based, non-IP based, and so forth.

Figure 2:
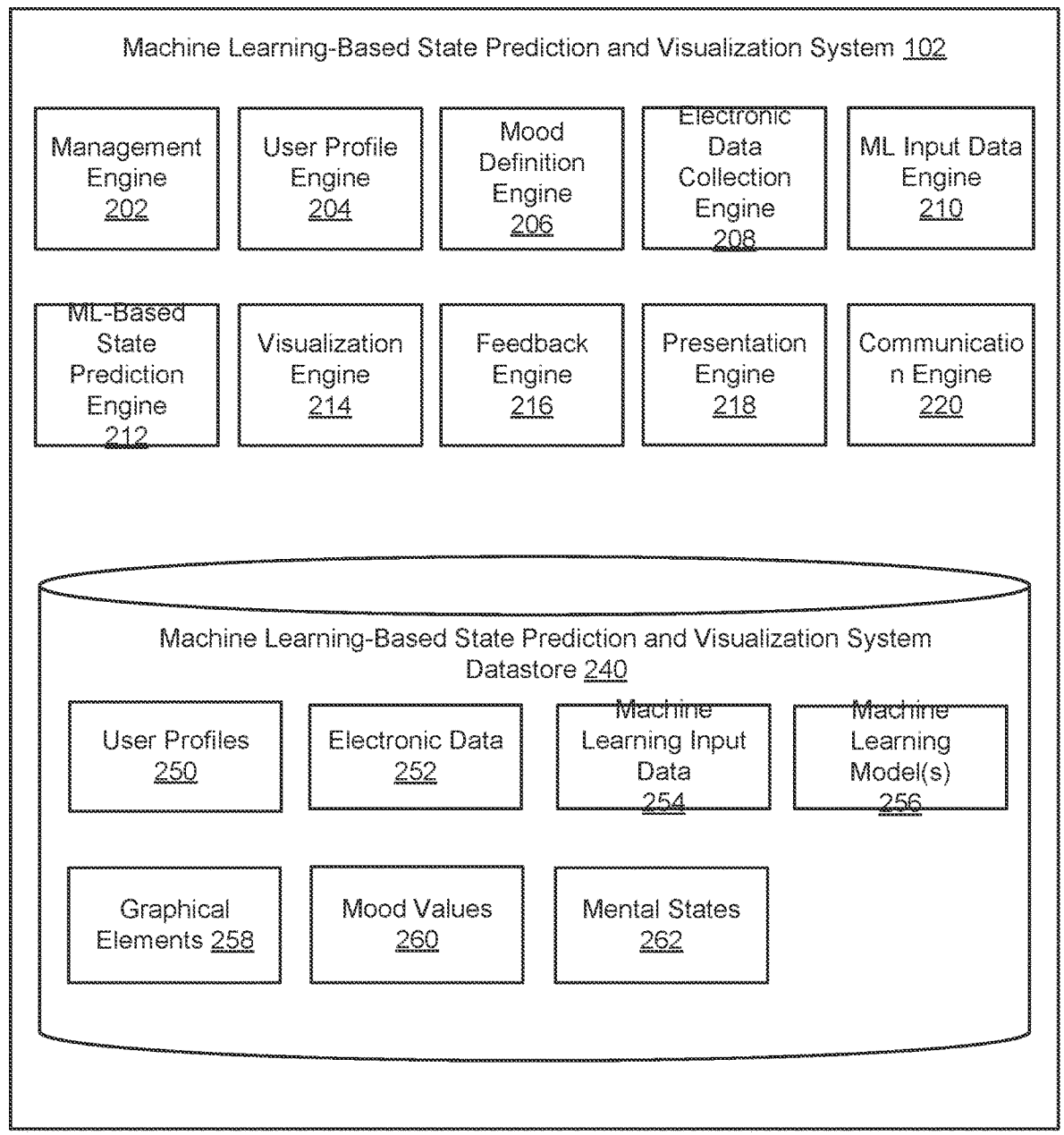
FIG. 2 depicts a diagram of an example machine learning-based state prediction and visualization system according to some embodiments.

FIG. 2 depicts a diagram of an example machine learning-based state prediction and visualization system 102 according to some embodiments. In the example of FIG. 2, the machine learning-based state prediction and visualization system 102 includes a management engine 202, a user profile engine 204, a mood definition engine 206, an electronic data collection engine 208, a machine learning input data 210, a machine learning-based state prediction engine 212, a visualization engine 214, a feedback engine 216, a presentation engine 218, a communication engine 220, and a machine learning-based state prediction and visualization system datastore 240.

The management engine 202 may function to manage (e.g., create, read, update, delete, or otherwise access) user profiles 250, electronic data 252, machine learning input data 254, machine learning model(s) 256, graphical elements 258, mood values 260 (or, simply, "moods"), and/or mental states 262. The management engine 202 can perform any of these operations manually (e.g., by a user interacting with a GUI) and/or automatically (e.g., triggered by one or more of the engines 204-220). Like the other engines described herein, some or all the functionality of the management engine 202 can be included in and/or cooperate with one or more other engines (e.g., engines 204-220) and datastores (e.g., machine learning-based state prediction and visualization system datastore 240).

The user profile engine 204 may function to register users (e.g., user "John Smith"), register associated user systems 104 (e.g., a mobile device of user John Smith), register user accounts (e.g., John Smith's accounts of third-party systems 106), and/or generate user profiles 250. User profiles 250 may include some or all of the following information:

User Profile Identifier: identifies the user profile.
User Identifier: identifies the user.
User Credentials: username, password, two-factor authentication, and/or other credentials.
User Personal Information: identifies the user's name, contact information (e.g., email address, phone number, mailing address).
Registered (or, associated) User Systems: Identifies user systems 104 associated with the user.
Registered (or, associated) Accounts and/or Third-Party Systems: identifies user accounts (e.g., social media accounts), and associated access information (e.g., APIs, user account names and credentials, and/or the like).
Mood History: History of identified moods for the user and associated time stamps.
Mental State History: history of mental states predicted by the machine learning-based state prediction and visualization system for the user, and associated timestamps.
Current Mental State: a current mental state of the user predicted by the machine learning-based state prediction and visualization system.
Historical User Selections: Historical selections of graphical elements selected by the user.
User Privacy Settings: identifies which electronic data 250, or types of electronic data (e.g., text messages), may be used for predicting mental state.
Electronic data: electronic data 252 obtained by the machine learning-based state prediction and visualization system 102, and/or references (e.g., pointers, links) to electronic data 252 obtained by the machine learning-based state prediction and visualization system.

In various embodiments, the user profiles 250 may be used by some or all of the engines 202-220 to perform their functionality described herein.

The mood definition engine 206 may function to define and/or generate moods. Moods may be identified by mood values. For example, mood values may be alphanumeric text describing a mood (e.g., "angry"), a numeric value, and/or hash values (e.g., for faster indexing, access, and/or the like). As used in this paper, moods are distinct from mental states. For example, moods may be discrete, while mental states may be contiguous, as discussed elsewhere in this paper. In some embodiments, the mood definition engine 206 defines moods as predetermined definitions that are generally accepted and understood. For example, the mood definition engine 206 may define an angry mood, a sad mood, a happy mood, and/or the like. These moods are discrete and have a generally understood definition.

Figure 5A:
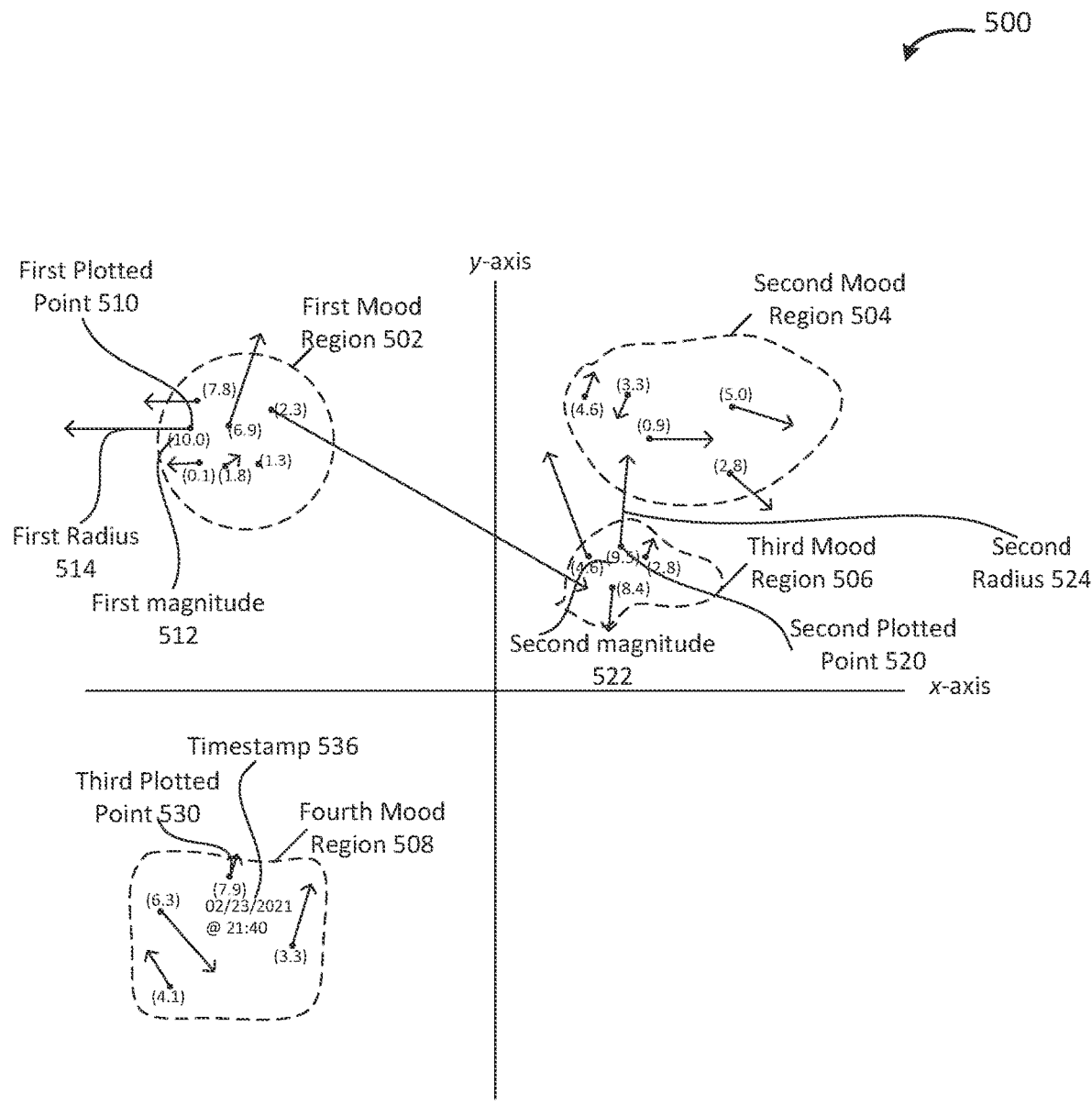
FIG. 5A depicts an example two-dimensional coordinate system representing an example mental state according to some embodiments.
Figure 5B:
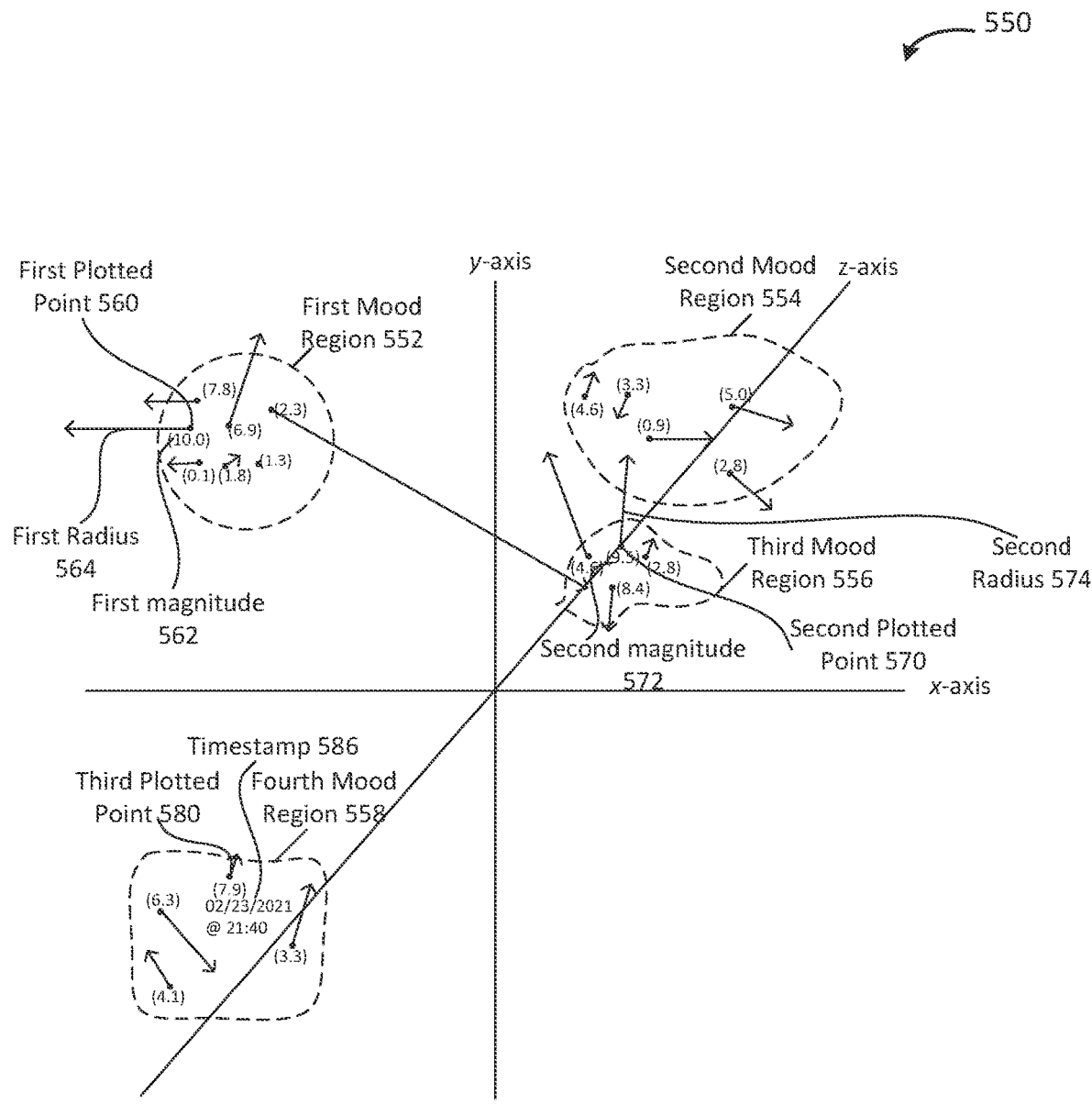
FIG. 5B depicts an example three-dimensional coordinate system representing an example mental state according to some embodiments.

In some embodiments, the mood definition engine 206 defines a mood as one or more regions of a coordinate system and/or space (or, simply, coordinate system). As used in this paper, coordinate systems are multi-dimensional (e.g., two-dimensional, three-dimensional, four-dimensional, and/or the like). In some embodiments, the boundaries of the regions may be manually defined and/or automatically defined by the mood definition engine 206. For example, an administrator may manually define the boundaries of the regions for some or all of the different moods. In another example, the mood definition engine 206 may automatically define mood regions based on known and/or labeled data (e.g., electronic data 252, machine learning input data 254). For example, data may be labeled for individuals with known moods, and those known moods may be plotted in the coordinate system. The plotted points may be used by the mood definition engine 206 to construct the boundaries of the mood regions. FIGS. 5A and 5B show example coordinate systems and example mood regions associated with different moods.

The electronic data collection engine 208 may function to collect, gather, and/or otherwise obtain electronic data 252 (e.g., from user systems 104 and/or third-party systems 106). For example, electronic data 252 may include texts messages (e.g., SMS messages, iMessages, and/or the like), email messages, social media data (e.g., data from a user's social media account), voice data (e.g., audio recording of a user speaking, voicemail messages, a phone or video call, and/or the like), image data (e.g., a picture of user, a video of a user), haptic data (e.g., pressure from user's hand holding a device), physical location data (e.g., GPS data), physical orientation data (e.g., a physical orientation of device of user at the time other electronic data is captured or other time), express statements by a user (e.g., an express indication of mood by a user in a text message or other electronic data 252), and/or the like.

In some embodiments, the electronic data collection engine 208 may scan associated user systems 104 for local electronic data 252 (e.g., text messages that are local to a user system 104, email messages that are local to a user system 104), remote electronic data 252 (e.g., cloud-stored text messages, cloud-stored email messages, social media data) to obtain the electronic data 252. The electronic data collection engine 208 may use information from an associated user profile 252 (e.g., user credentials) and/or APIs to obtain the electronic data 252. For example, the electronic data collection engine 208 may use APIs to obtain electronic data 252 from Facebook, email servers, text message servers, and/or the like, in addition to obtaining data stored locally on user systems 104. In some embodiments, the electronic data 252 obtained by the electronic data collection engine 208 for various users may be limited and/or otherwise controlled by associated user profiles 250. For example, a user may specify in the privacy settings of their user profile 250 that only local data may be used, only data to or from certain recipients may be used, only data from a certain time period may be used, only specifically selected data or types of data (e.g., text messages) may be used, and/or the like.

In some embodiments, the electronic data collection engine 208 may obtain electronic data 252 in real-time and/or periodically. For example, the electronic data collection engine 208 may obtain electronic data 252 as it is entered by a user (e.g., as a user inputs a text message into a user system 104). In another example, the electronic data collection engine 208 may periodically obtain (e.g., once an hour, once a day, and/or the like) electronic data 252. It will be appreciated that obtaining the electronic data 252 may comprise obtaining the actual original electronic data, a copy of the original electronic data, a reference (e.g., pointer, link) to the original electronic data, a reference to a copy of the original electronic data, and/or the like. Accordingly, it will be appreciated that references to electronic data may be operated on by the machine learning-based state prediction and visualization system 102 to achieve the same or similar results as operating on the actual electronic data 252 itself.

In some embodiments, the electronic data collection engine 208 may collect electronic data 252 directly from a user (e.g., an explicit indication of a mood). For example, the electronic data collection engine 208 may prompt the user for their mood in response to a trigger event. For example, trigger events may be based on identified keywords of electronic data 252, time-based triggers, and/or the like. In another example, a user may initiate providing an explicit indication of their mood to the machine learning-based state prediction and visualization system 102.

In some embodiments, a user system (e.g., user system 104) includes some or all of the functionality of the electronic data collection engine 208 and/or functions to cooperate with the electronic data collection engine 208 to perform some or all of the functionality thereof. For example, an application (e.g., mobile application) executing on a user system 104 may itself, and/or in cooperation with the electronic data collection engine 208, obtain electronic data 252. Similarly, in some embodiments, functionality of other engines and/or components of the machine learning-based state prediction and visualization system 102 can be performed by one or more other systems (e.g., user systems 104) and/or in cooperation with those one or more other systems. In some embodiments, the machine learning-based state prediction and visualization system 102 comprises a server system and the user systems 104 comprise client systems of the machine learning-based state prediction and visualization system 104. In some embodiments, some or all of the functionality of the machine learning-based state prediction and visualization system 104 can be implemented as part of a user system (e.g., as a mobile application executing the user system 104).

The machine learning input data engine 210 may function to generate input data 254 for one or machine learning models 256. The machine learning input data engine 210 may generate the machine learning input data 254 based on some or all of the electronic data 252. For example, the machine learning input data engine 210 may generate machine learning input data 254 based on some or all of the electronic data 252 associated with a particular user (e.g., user John Smith). In some embodiments, the machine learning input data engine 210 may normalize the electronic data 252 to a normalized data format, and the normalized data format may comprise the data format of the machine learning input data 254. This may allow, for example, the machine learning-based state prediction and visualization system 102 to obtain data from a variety of different sources regardless of their original format and allow the machine learning-based state prediction and visualization system 102 to operate on the data regardless of the original format.

In some embodiments, the machine learning input data engine 210 selects a subset of electronic data 252 associated with a particular user. For example, the machine learning input data engine 210 may select the subset of electronic data 252 based on privacy setting of an associated user profile 250. In another example, the machine learning input data 210 may select representative electronic data 252 in order to reduce an amount of data provided to the machine learning model 256, and/or prevent or reduce the likelihood of providing stale data to the machine learning model 256. For example, the machine learning input data engine 210 may perform the selection based on user history. Accordingly, the machine learning input data engine 210 may select only electronic data 252 within the past month for one user (e.g., because there is a relatively large amount of data for that user), while the machine learning input data engine 210 may select data within the past year for another user (e.g., because there is a relatively little amount of data for that user).

In some embodiments, the machine learning input data engine 210 may select a subset of electronic data 252 based on one or more rules. For example, rules may define time periods of data to be used (e.g., within the last month), type of data to be used (e.g., only text messages), and/or the like. Different rules may be manually and/or automatically defined for different users. For example, based on the feedback received from particular users (as discussed elsewhere herein), the machine learning input data engine 210 may determine that particular types are electronic data 252 (e.g., email messages) are not effective in predicting mental state for a particular user, while feedback received from other users may indicate that those types of electronic data 252 are effective in predicting mental state for other users. Accordingly, the machine learning input data engine 210 may filter out ineffective types of electronic data 252 for some users, while not filtering those types of electronic data 252 for other users.

In some embodiments, the machine learning input data engine 210 may identify, define, determine, and/or analyze (collectively, analyze) features of electronic data 252 to predict mental state. For example, the machine learning-based state prediction engine 212 may analyze features of voice data of electronic data 252 to predict mental state. Voice data may include recordings of phone or video calls, voicemail messages, ambient voice data (e.g., of the user speaking in the vicinity of a user system 104 that may capture the voice data), and/or the like. The machine learning input data engine 210 may analyze features of the voices in the voice data (e.g., voice of the user and/or others) to identify stress, tension, moods, and/or the like. For example, the machine learning input data engine 210 may include digital signal processing elements in order to facilitate analysis of voice data and/or other electronic data 252. This analysis and/or features may be used by the machine learning model 256 to facilitate prediction of a user's mental state.

In another example, the machine learning input data engine 210 may analyze image data (e.g., pictures or video of a user or other individuals, such as individuals the user is communicating with) to predict mental state. In some embodiments, the machine learning input data engine 210 may use digital signal processing and/or facial recognition to scan images for features indicating stress, tension, moods, and/or the like. This analysis and/or features may be used by the machine learning model 256 to facilitate prediction of a user's mental state.

In another example, the machine learning input data engine 210 may include optical character recognition, regular expressions, and/or natural language processing elements to facilitate mental state prediction. For example, optical character recognition, regular expressions, and/or natural language processing elements may be used to analyze features of a text messages, email messages, social media data, and/or the like, to facilitate prediction of mental state.

The machine learning-based state prediction engine 212 may function to predict mental states of users. In some embodiments, the machine learning-based state prediction engine 212 predicts mental state using one more machine learning models 256 and machine learning input data 254. For example, the machine learning models 256 may include Bayesian models, neural networks models, deep learning models, supervised learning models, unsupervised learning models, random forest models, and/or the like.

In one example, the system can have a distribution of moods with magnitudes and uncertainties at one point in time. In some embodiments, the mental states can be temporal representations of such distributions at several different points in time. Accordingly, such mental states can efficiently capture both the time scope of complex behaviors as well as any relevant uncertainties.

In some embodiments, a mental state may be defined as a set of mood values, a set of uncertainty values, and a set of a magnitude values. Each mood value of the set of mood values may be associated with a corresponding uncertainty value of the set of uncertainty values and a corresponding magnitude value of the set of magnitude values. The magnitude value may indicate a relative strength and/or weakness of the associated mood value. In some embodiments, a predicted mental state of the user (e.g., at a particular point of time and/or a particular period of time) may be stored in a user profile 250 and/or the datastore 240 as mental states 262. The aforementioned definition of a mental state is one example of a mental state, and may be referred to as one example of a triplet. The triplet may be stored in a data object, and/or as table data. In some embodiments, triplets may be stored in a dynamic data object. For example, the dynamic data object may automatically resize depending on the amount of triplet data being stored. This may allow, for example, the machine learning-based state prediction and visualization system to function more efficiently.

In some embodiments, the mental state is defined as a mapping of the triplet to a coordinate system. For example, each mood of the triplet may be plotted in various mood regions of the coordinate system, and the distribution of those plots over time may be the predicted mental state of a user. Each mood may be associated with a particular point in time (e.g., as captured by a timestamp). Accordingly, a mental state may be considered to be contiguous, while a mood may be considered to be discrete. Furthermore, while moods are typically predefined, mental states typically are not predefined. For example, while the machine learning-based state prediction engine 212 may recognize and/or define general categories of mental state (e.g., depressed, bipolar, and/or the like), the predicted mental states themselves may be unique. Accordingly, two different users may have different mental states (e.g., as indicated by their respective mappings) but fall within the same category of mental state (e.g., depressed). This may be significant because the selection and arrangement of graphical elements, as discussed elsewhere herein, may be based on the predicted mental state of the user, and not necessarily upon an associated category of mental state. Accordingly, two users that may be predicted to fall into a depressed category, may nonetheless be presented with a different selection and/or arrangement of graphical elements. In other embodiments, graphical elements may be presented based on a category of mental state instead of, or in addition to, the predicted mental state.

In some embodiments, the uncertainty value represents a predicted accuracy value of the associated mood value. For example, an uncertainty value may be a numerical value (e.g., between 0-10), a percentage value, and/or the like. The uncertainty value may range from no uncertainty (e.g., because the user expressly indicated that they are angry) to highly uncertain (e.g., there was a relatively small amount of electronic data 252 or machine learning input data 254). In some embodiments, the uncertainty value may be referred to as a variance, and it may be represented as a radius (or, radii) originating from the corresponding plotted point associated with the mood. The uncertainty value may be represented as a feature of the mapped radius. For example, a shorter length radius may indicate a lower uncertainty value, and a longer length radius may indicate a higher uncertainty value.

In some embodiments, the machine learning-based state prediction engine 212 may predict uncertainty values based on the machine learning input data 254. If there is a relatively large amount of machine learning input data 254 to be provided to the machine learning model 256 to predict the user's mental state, the uncertainty values may be relatively low. Conversely, if there is a relatively small amount of machine learning input data 254 to be provided to the machine learning model 256 to predict the user's mental state, the uncertainty values may be relatively high. Similarly, if the machine learning model 256 has a relatively large amount of labeled data similar to machine learning input data 254, then uncertainty values may be relatively low, while if the machine learning model 256 has a relatively small amount of labeled data similar to the machine learning input data 254, then the uncertainty values may be relatively high.

In some embodiments, plotted points that indicate a user's mood (e.g., for the purpose of predicting the user's mental state) may be referred to as "user points" of the coordinate system. The coordinate system may also include other plotted points, as well. For example, the coordinate system may include plotted points of moods of other individuals (e.g., based on labeled data). The distance between a user point and another plotted point may be used to predict and/or adjust the uncertainty value. For example, a user point near another plotted point may be assumed to be more accurate, and may result in a lower uncertainty value, while a user point relatively far away from another plotted point may be assumed to be less accurate and may result in a higher uncertainty value.

In some embodiments, the radius representing the uncertainty value may extend from a point in a particular mood region (e.g., an angry region) into one or more other mood regions (e.g., a sad region). In such instances, this may allow the machine learning-based state prediction engine 212 to base the mental state prediction not only on the plotted mood region (e.g., angry mood region), but also on the one or more other mood regions as well (e.g., the sad mood region).

In some embodiments, the magnitude value may be a numerical value (e.g., between 0-10), a percentage value, and/or the like. As indicated elsewhere herein, the magnitude value may indicate a relative strength and/or weakness of an associated mood. For example, a mental state may include an angry mood value with relatively high magnitude (e.g., 8 on a scale of 0-10), and a relatively low uncertainty value (e.g., 2 on a scale of 0-10). Accordingly, anger may be relatively larger impact on the overall predicted mental state relative to other moods of the user that have lower magnitudes and/or higher uncertainty values.

In some embodiments, a mental state may include a second uncertainty value representing a predicted accuracy of an associated magnitude value. This second uncertainty value may be mapped to a coordinate system as a second radius (or radii) originating from the plotted user point.

In some embodiments, the machine learning-based state prediction engine 212 may output one or more vector values (e.g., output from a machine learning model 256) corresponding to a triplet. The machine learning-based state prediction engine 212 may map a triplet to a coordinate system. In some embodiments, the mapping of a triplet to a coordinate system is a mental state. In other embodiments, the triplet itself is a mental state.

In some embodiments, the machine learning-based state prediction engine 212 may predict mental state based on physical orientation of a user system 104. The physical orientation may include angle, tilt, and/or the like, relative to the user and/or another feature (e.g., another person in which a user is communicating, or the ground surface). For example, if the physical orientation indicates that a top portion of a user system 104 is points towards the ground, the machine learning-based state prediction engine 212 may use that as an indicator of one or more particular moods (e.g., a sad mood), while a physical orientation of a top portion of the user system 104 pointing away from the ground may be used as an indicate of one or more other moods (e.g., a happy mood).

The visualization engine 214 may function to select, arrange, and/or otherwise organize (collectively, organize) graphical elements (e.g., emojis) based on predicted mental state. For example, graphical elements may be static, animated, include audio elements, video elements, haptic elements, and/or the like. In some embodiments, the visualization engine 214 may organize a subset of graphical elements from a set of graphical elements based on a mental state of a user in order to present an intelligently and computationally efficient organization of graphical elements through a graphical user interface (e.g., a text message interface of a text messaging application executing on a user system 104). More specifically, the visualization engine 214 may organize graphical elements based on a triplet and/or a mapping of a triplet on a coordinate system.

As discussed elsewhere herein, mental states typically are not predefined. For example, while the machine learning-based state prediction engine 212 may recognize and/or define general categories of mental state (e.g., depressed, bipolar, and/or the like), the predicted mental states themselves may be unique. Accordingly, two different users may have different mental states (e.g., as indicated by their respective mappings) but fall within the same category of mental state (e.g., depressed). The visualization engine 214 may organize the subset of graphical elements based on the predicted mental state of the user, and not necessarily upon associated category of mental state. Thus, two different users that may be predicted to fall into a "depressed" mental category, may nonetheless be presented with a different organization of graphical elements.

In some embodiments, the visualization engine 214 may use an additional layer of machine learning to organize graphical elements. For example, a first layer of machine learning may be used by the machine learning-based state prediction engine 212 to predict mental state, while a second layer of machine (e.g., using different and/or the same machine learning model 256 as the machine learning-based state prediction engine 212) may be used to organize graphical elements based on the predicted mental state. For example, a predicted mental state 260 may be provided as input to a second machine learning model 256, and the output may comprise a vector value that may be used to organize a subset of graphical elements. In some embodiments, the second model may be based on labeled data associating particular graphical elements with particular predicted mental states that have been verified (e.g., manually prior to model deployment and/or by the feedback engine 216, discussed below).

The feedback engine 216 may function to train, refine, and/or otherwise improve the machine learning and/or machine learning models 256 described herein. In some embodiments, the feedback engine 216 receives user selections of graphical elements presented to a user based on the user's predicted mental state. For example, a user selection from a subset of graphical elements presented to the user based on their predicted mental state may indicate that the machine learning model is performing accurately. In another example, a user selection of a graphical element that was not included in the subset of graphical elements presented to the user based on their predicted mental state may indicate that the machine learning model needs improvement and/or correction (e.g., due to concept drift). The feedback engine 216 may utilize the user selections to adjust parameters of the machine learning model 256, and/or otherwise train, retrain, refine, and/or improve the corresponding machine learning and/or machine learning models 256.

The presentation engine 218 may function to present visual, audio, and/or haptic information. In some embodiments, the presentation engine 218 generates graphical user interfaces, and/or components thereof (e.g., server-side graphical user interface components) that can be rendered as complete graphical user interfaces on remote systems (e.g., user systems 104).

The communication engine 220 may function to send requests, transmit and receive communications, and/or otherwise provide communication with one or more of the systems, engines, devices and/or datastores described herein. In a specific implementation, the communication engine 220 may function to encrypt and decrypt communications. The communication engine 220 may function to send requests to and receive data from one or more systems through a network or a portion of a network (e.g., communication network 108). In a specific implementation, the communication engine 220 may send requests and receive data through a connection, all or a portion of which can be a wireless connection. The communication engine 220 may request and receive messages, and/or other communications from associated systems and/or engines. Communications may be stored in the machine learning-based state prediction and visualization system datastore 240.

Figure 3:
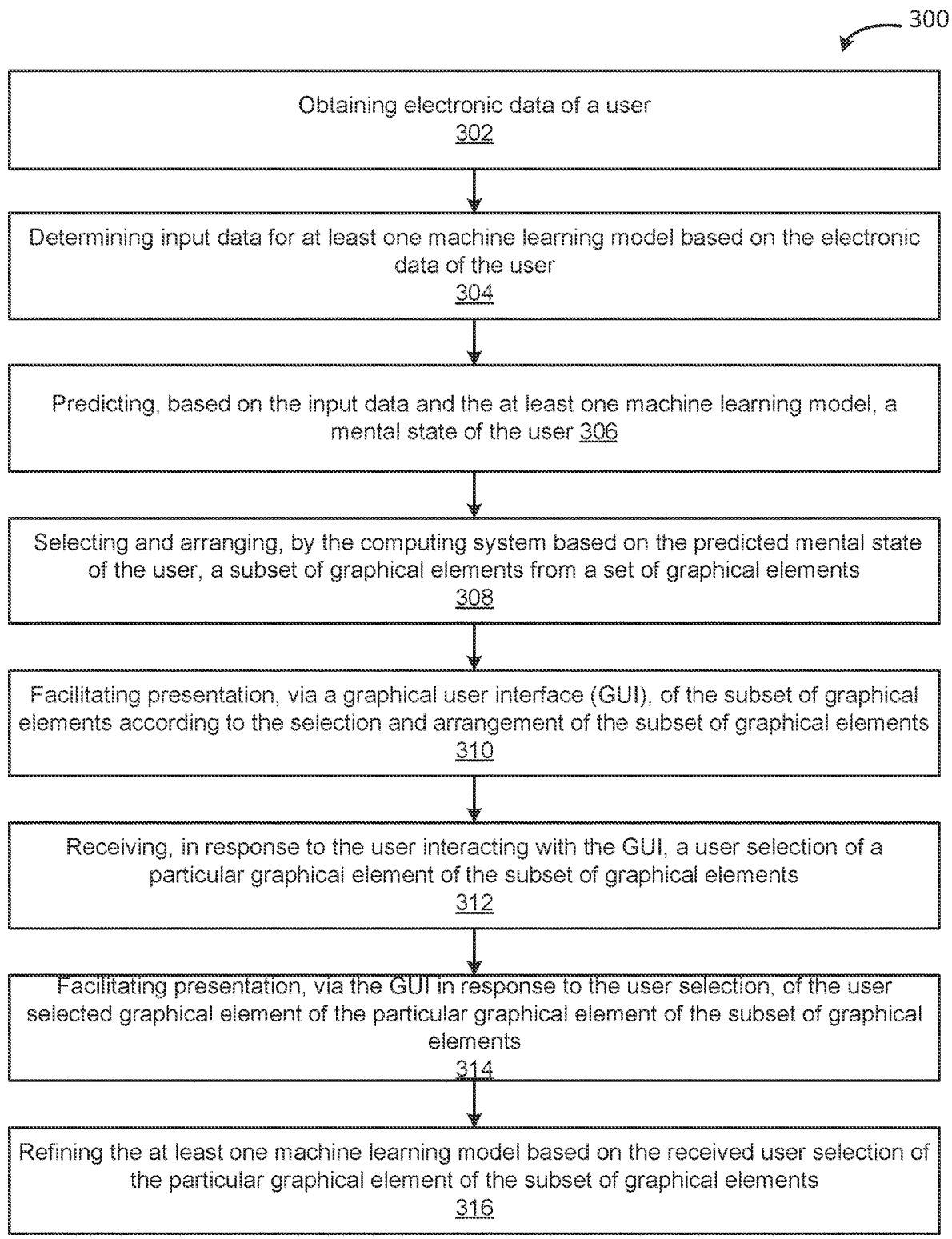
FIG. 3 depicts a flowchart of an example of a method of predicting mental state of a user using machine learning and selecting and arranging graphical elements based on the user's predicted mental state according to some embodiments.

FIG. 3 depicts a flowchart of an example of a method 300 of predicting mental state of a user using machine learning and selecting and arranging graphical elements based on the user's predicted mental state according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 302, a machine learning-based state prediction and visualization system (e.g., machine learning-based state prediction and visualization system 102) obtains electronic data (e.g., electronic data 252) of a user (e.g., user system 104 and/or a user of a user system 104). In some embodiments, a communication engine (e.g., communication engine 220) and/or an electronic data collection engine (e.g., electronic data collection engine 208) obtains the electronic data over a communication network (e.g., communication network 108) from one or more user systems (e.g., user systems 104) and/or one or more third-party systems (e.g., third-party systems 106). A management engine (e.g., management engine 202) may store the electronic data in a datastore (e.g., machine learning-based state prediction and visualization system datastore 240).

In step 304, the machine learning-based state prediction and visualization system determines input data (e.g., machine learning input data 254) for at least one machine learning model (e.g., at least one machine learning model 256) based on the electronic data of the user. In some embodiments, a machine learning input data engine (e.g., machine learning input data engine 210) determines the input data.

In step 306, the machine learning-based state prediction and visualization system predicts, based on the input data and the at least one machine learning model (e.g., the input data may be provided as input to the machine learning model), a mental state of the user. The mental state may comprise a set of mood values (e.g., mood values 260), a set of uncertainty values, and a set of a magnitude values. Each mood value of the set of mood values may be associated with a corresponding uncertainty value of the set of uncertainty values and a corresponding magnitude value of the set of magnitude values. The magnitude value may indicate a relative strength and/or weakness of the associated mood value. In some embodiments, a machine learning-based state prediction engine (e.g., machine learning-based state prediction engine 212) performs the prediction. In some embodiments, the predicted mental state of the user (e.g., at a particular point of time and/or a particular period of time) may be stored by the management engine in a user profile (e.g., a user profile 250) and/or the datastore.

In step 308, the machine learning-based state prediction and visualization system selects and/or arranges, based on the predicted mental state of the user, a subset of graphical elements (e.g., graphical elements 258) from a set of graphical elements. For example, the graphical elements may be emojis. Each graphical element of the set of graphical elements may be associated (e.g., linked) with a corresponding mood value of the set of mood values. Each graphical element of the subset of graphical elements may be associated with the predicted mental state of the user. In some embodiments, a visualization engine (e.g., visualization engine 214) selects and/or arranges the graphical elements based on the mental state of the user (e.g., at one or more points of time and/or one or more periods of time).

In step 310, the machine learning-based state prediction and visualization system facilitates presentation (e.g., display), via a graphical user interface (GUI), of the subset of graphical elements according to the selection and arrangement of the subset of graphical elements. For example, the machine learning-based state prediction and visualization system may cause an associated device (e.g., a user system 104 of the user) to display the subset of graphical elements according to the selection and arrangement of the subset of graphical elements. In some embodiments, a presentation engine (e.g., presentation engine 218) and/or the visualization engine facilitates the presentation of the selection and arrangement of the graphical elements.

In step 312, the machine learning-based state prediction and visualization system receives, in response to the user interacting with the GUI presenting the subset of graphical elements according to the selection and arrangement of the subset of graphical elements, a user selection of a particular graphical element of the subset of graphical elements. For example, a user may select a particular graphical element displayed on their user system, and the selection may be communicated from the user system over the communication network to the communication engine, and the communication engine may then route the received selection to the presentation engine and/or the visualization engine. In some embodiments, the received selection may be used by a feedback engine (e.g., for example, 216) to refine, train, and/or otherwise improve the machine learning model and/or the machine learning-based state prediction engine.

In step 314, the machine learning-based state prediction and visualization system facilitates presentation (e.g., display), via the GUI in response to the user selection, of the user selection of the particular graphical element of the subset of graphical elements. In some embodiments, the presentation engine and/or visualization engine facilitates the presentation of the user selected graphical element.

In step 316, the machine learning-based state prediction and visualization system refines the at least one machine learning model based on the received user selection. In some embodiments, a feedback engine (e.g., feedback engine 216) refines the at least one machine learning model.

In some embodiments, step 312, like any of the other steps, may be optional. For example, step 314 may facilitate presentation of the particular graphical element in response to a user selection received at the user system (e.g., without the machine learning-based state prediction and visualization system receiving the user selection).

FIG. 4 depicts a flowchart of an example of a method 400 of mental state prediction according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 402, a machine learning-based state prediction and visualization system (e.g., machine learning-based state prediction and visualization system 102) maps a set of mood values (e.g., mood values 260), the set of uncertainty values, and the set of magnitude values to a coordinate system. The coordinate system may comprise a plurality of different mood regions. Each of the set of mood values may be mapped to the coordinate system as a corresponding user point in the coordinate system. Each of the corresponding uncertainty values may be mapped as a corresponding radius originating at the corresponding point in the coordinate system. In some embodiments, a machine learning-based state prediction engine (e.g., machine learning-based state prediction engine 212) and/or visualization engine 214 performs the mapping. In some embodiments, a mental state is defined by the mapping of step 402 (and/or other mappings described herein) and/or vice versa. Accordingly, in some instances, a user may have a unique mental state (e.g., different from any other user or previously known or defined mental state).

In step 404, the machine learning-based state prediction and visualization system identifies at least a first mood region of the plurality of different mood regions that includes at least one corresponding user mapped therein. In some embodiments, the machine learning-based state prediction engine and/or visualization engine performs the identification.

In step 406, the machine learning-based state prediction and visualization system identifies at least a second mood region of the plurality of different mood regions that does not include any corresponding user points mapped therein, and also includes at least a portion of a first radius of the corresponding radii mapped in the coordinate system. In some embodiments, the machine learning-based state prediction engine and/or visualization engine performs the identification.

In some embodiments, the mental state of the user is predicted based on the mood regions identified in steps 404 and 406, as well as the magnitude values associated with the at least one corresponding user point mapped in the at least a first mood region of the plurality of different moods regions and the first radius of the corresponding radii mapped in the coordinate system.

FIG. 5A depicts an example two-dimensional coordinate system 500 representing an example mental state according to some embodiments. The two-dimensional coordinate system 500 may be generated by the machine learning-based state prediction and visualization system 102. In some embodiments, the two-dimensional coordinate system 500 may be represented by one or more graphical user interfaces (e.g., generated by the machine learning-based state prediction and visualization system 102 and/or user systems 104).

As shown, the two-dimensional coordinate system 500 includes two-axes (e.g., the x-axis and the y-axis). The plotted points (e.g., first plotted point 510, second plotted point 520, and third plotted point 530) may represent respective moods at different times for an individual. For example, one individual may be associated with multiple points (e.g., first plotted point 512 and second plotted point 522) that each represent a particular mood at a particular point in time. The mental state may comprise the set of those plotted points. The points may be plotted in various mood regions of the two-dimensional coordinate system 500. For example, the mood regions may include a first mood region 502 (e.g., a happy mood region), a second mood region 504 (e.g., a sad mood region), a third mood region 506 (e.g., an angry mood region), and a fourth mood region 508. Each point may be associated with a magnitude value (e.g., 1.3 on a scale of 0.0 to 10.0, with 10.0 being the highest value indicating the strongest mood) and a radius indicating an uncertainty value associated with the plotted point. For example, a longer radius may indicate a higher uncertainty in the predicted mood and/or plotted point, and a short radius may indicate a lower uncertainty. In some examples, a plotted point may effectively overlap multiple mood regions based on the associated uncertainty value. For example, the second plotted point 520 has a magnitude value 522 of 9.5, and a radius 524 that extends into the second mood region.

FIG. 5B depicts an example three-dimensional coordinate system 550 representing an example mental state according to some embodiments. The three-dimensional coordinate system 550 may be generated by the machine learning-based state prediction and visualization system 102. In some embodiments, the three-dimensional coordinate system 550 may be represented by one or more graphical user interfaces (e.g., generated by the machine learning-based state prediction and visualization system 102 and/or user systems 104).

As shown, the three-dimensional coordinate system 550 includes three-axes (e.g., the x-axis, the y-axis, and the z-axis). The plotted points (e.g., first plotted point 560, second plotted point 570, and third plotted point 580) may represent respective moods at different times for an individual. For example, one individual may be associated with multiple points (e.g., first plotted point 562 and second plotted point 572) that each represent a particular mood at a particular point in time. The mental state may comprise the set of those plotted points associated with that individual. The points may be plotted in various mood regions of the three-dimensional coordinate system 550. For example, the mood regions may include a first mood region 552 (e.g., a happy mood region), a second mood region 554 (e.g., a sad mood region), a third mood region 556 (e.g., an angry mood region), and a fourth mood region 558. Each point may be associated with a magnitude value (e.g., 1.3 on a scale of 0.0 to 10.0, with 10.0 being the highest value indicating the strongest mood) and a radius indicating an uncertainty value associated with the plotted point. For example, a longer radius may indicate a higher uncertainty in the predicted mood and/or plotted point, and a short radius may indicate a lower uncertainty. In some examples, a plotted point may effectively overlap multiple mood regions based on the associated uncertainty value. For example, the second plotted point 570 has a magnitude value 572 of 9.5, and a radius 574 that extends into the second mood region.

It will be appreciated that the elements of the three-dimensional coordinate system 550 are represented with two-dimensional drawings for illustrative purposes. It will be appreciated that in some embodiments, each of the elements of FIG. 5B (e.g., mood regions, plotted points, radii, and/or the like) may be represented in three-dimensions instead of, or in addition to, two-dimensions.

Figure 6:
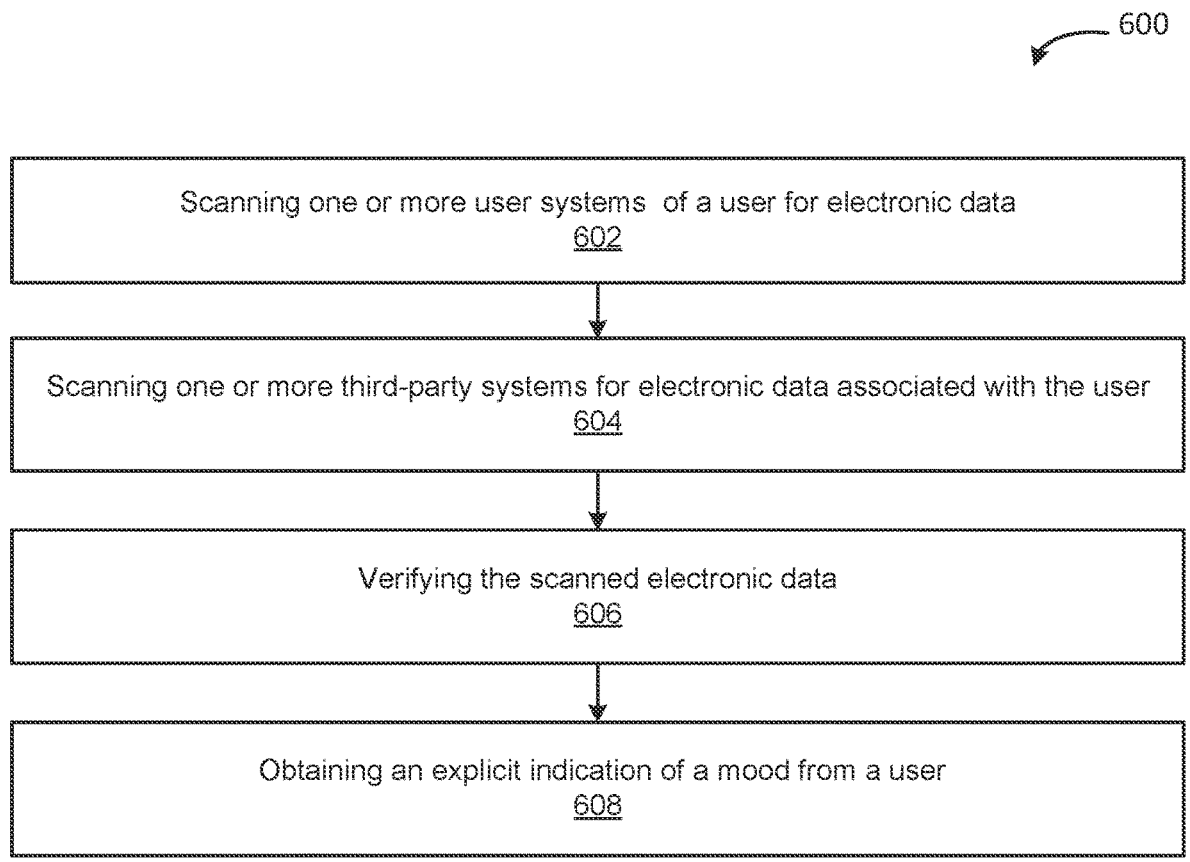
FIG. 6 depicts a flowchart of an example of a method of collecting electronic data of a user according to some embodiments.

FIG. 6 depicts a flowchart of an example of a method 600 of collecting electronic data of a user according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 602, a machine learning-based state prediction and visualization system (e.g., machine learning-based state prediction and visualization system 102) scans one or more user systems (e.g., one or more user systems 104) of a user for electronic data (e.g., electronic data 252). In some embodiments, an electronic data collection engine (e.g., electronic data collection engine 208) performs the scan.

In step 604, the machine learning-based state prediction and visualization system scans one or more third-party systems (e.g., third-party systems 106) for electronic data associated with the user. For example, the machine learning-based state prediction and visualization system may scan social media accounts of the user for electronic data associated with the user. In some embodiments, the electronic data collection engine performs the scan.

In step 606, the machine learning-based state prediction and visualization system verifies whether the electronic data identified by the scans of step 602 and/or 604 may be used for mental state prediction of the user, and if so, verifies which electronic data may be used (e.g., certain data or all data). For example, the machine learning-based state prediction and visualization system may prompt the user for verification. In another example, the machine learning-based state prediction and visualization system may check the user's associated user profile (e.g., user profile 250) to determine verification. Verification may be performed before, during, or after a scan. In some embodiments, electronic data collection engine performs the verification(s).

In step 608, the machine learning-based state prediction and visualization system obtains an explicit indication of a mood from a user. For example, the machine learning-based state prediction and visualization system may prompt the user for their mood in response to a trigger event. In another example, a user may initiate providing an explicit indication of their mood to the machine learning-based state prediction and visualization system. In some embodiments, the electronic data collection engine obtains the explicit indication of mood from the user.

Figure 7:
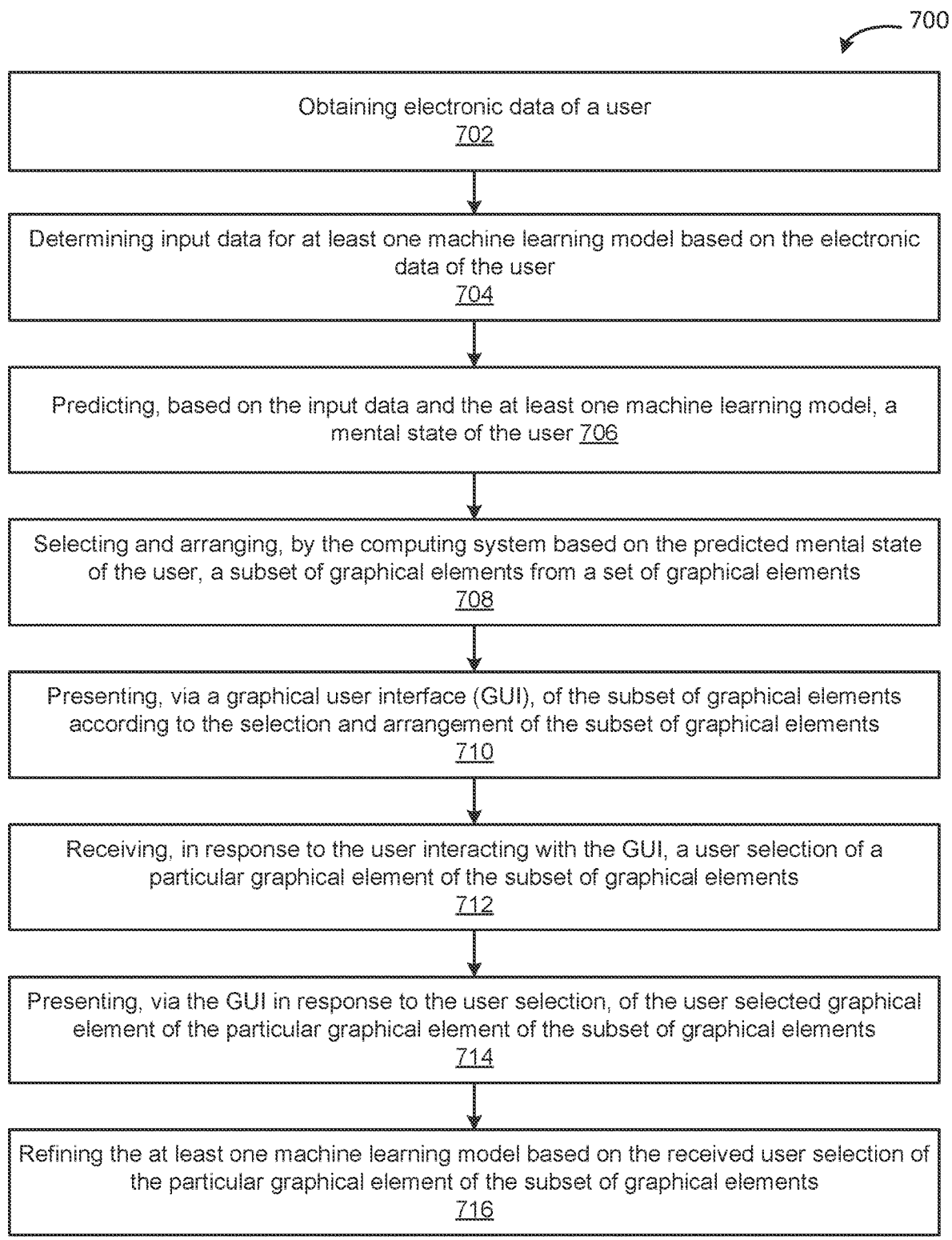
FIG. 7 depicts a flowchart of an example of a method of predicting mental state of a user using machine learning and selecting and arranging graphical elements based on the user's predicted mental state according to some embodiments.

FIG. 7 depicts a flowchart of an example of a method 700 of predicting mental state of a user using machine learning and selecting and arranging graphical elements based on the user's predicted mental state according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 702, a machine learning-based state prediction and visualization system (e.g., machine learning-based state prediction and visualization system 102) obtains electronic data (e.g., electronic data 252) of a user (e.g., user system 104 and/or a user of a user system 104). In some embodiments, a communication engine (e.g., communication engine 220) and/or an electronic data collection engine (e.g., electronic data collection engine 208) obtains the electronic data over a communication network (e.g., communication network 108) from one or more user systems (e.g., user systems 104) and/or one or more third-party systems (e.g., third-party systems 106). A management engine (e.g., management engine 202) may store the electronic data in a datastore (e.g., machine learning-based state prediction and visualization system datastore 240).

In step 704, the machine learning-based state prediction and visualization system determines input data (e.g., machine learning input data 254) for at least one machine learning model (e.g., at least one machine learning model 256) based on the electronic data of the user. In some embodiments, a machine learning input data engine (e.g., machine learning input data engine 210) determines the input data.

In step 706, the machine learning-based state prediction and visualization system predicts, based on the input data and the at least one machine learning model, a mental state of the user. The mental state may comprise a set of mood values (e.g., mood values 260), a set of uncertainty values, and a set of a magnitude values. Each mood value of the set of mood values may be associated with a corresponding uncertainty value of the set of uncertainty values and a corresponding magnitude value of the set of magnitude values. The magnitude value may indicate a relative strength and/or weakness of the associated mood value. In some embodiments, a machine learning-based state prediction engine (e.g., machine learning-based state prediction engine 212) performs the prediction. In some embodiments, the predicted mental state of the user (e.g., at a particular point of time and/or a particular period of time) may be stored by the management engine in a user profile (e.g., a user profile 250) and/or the datastore.

In step 708, the machine learning-based state prediction and visualization system selects and/or arranges, based on the predicted mental state of the user, a subset of graphical elements (e.g., graphical elements 258) from a set of graphical elements. For example, the graphical elements may be emojis. Although method 700 uses graphical elements, it will be appreciated that the method 700 may also use other types of elements (e.g., other types of emotional indicators) instead of, or in addition to, graphical elements. Each graphical element of the set of graphical elements may be associated (e.g., linked) with a corresponding mood value of the set of mood values. Each graphical element of the subset of graphical elements may be associated with the predicted mental state of the user. In some embodiments, a visualization engine (e.g., visualization engine 214) selects and/or arranges the graphical elements based on the mental state of the user (e.g., at one or more points of time and/or one or more periods of time).

In step 710, the machine learning-based state prediction and visualization system presents (e.g., displays), via a graphical user interface (GUI), the subset of graphical elements according to the selection and arrangement of the subset of graphical elements. For example, the machine learning-based state prediction and visualization system may cause an associated device (e.g., a user system 104 of the user) to display the subset of graphical elements according to the selection and arrangement of the subset of graphical elements. In some embodiments, a presentation engine (e.g., presentation engine 218) and/or the visualization engine facilitates the presentation of the selection and arrangement of the graphical elements.

In step 712, the machine learning-based state prediction and visualization system receives, in response to the user interacting with the GUI presenting the subset of graphical elements according to the selection and arrangement of the subset of graphical elements, a user selection of a particular graphical element of the subset of graphical elements. For example, a user may select a particular graphical element displayed on their user system, and the selection may be communicated from the user system over the communication network to the communication engine, and the communication engine may then route the received selection to the presentation engine and/or the visualization engine. In some embodiments, the received selection may be used by a feedback engine (e.g., for example, 216) to refine, train, and/or otherwise improve the machine learning model and/or the machine learning-based state prediction engine.

In step 714, the machine learning-based state prediction and visualization system presents (e.g., displays), via the GUI in response to the user selection, the user selected graphical element of the particular graphical element of the subset of graphical elements. In some embodiments, the presentation engine and/or visualization engine facilitates the presentation of the user selected graphical element.

In step 716, the machine learning-based state prediction and visualization system refines the at least one machine learning model based on the received user selection. In some embodiments, a feedback engine (e.g., feedback engine 216) refines the at least one machine learning model.

In some embodiments, step 712, like any of the other steps, may be optional. For example, step 714 may present the particular graphical element in response to a user selection received at the user system (e.g., without the machine learning-based state prediction and visualization system receiving the user selection).

Figure 8:
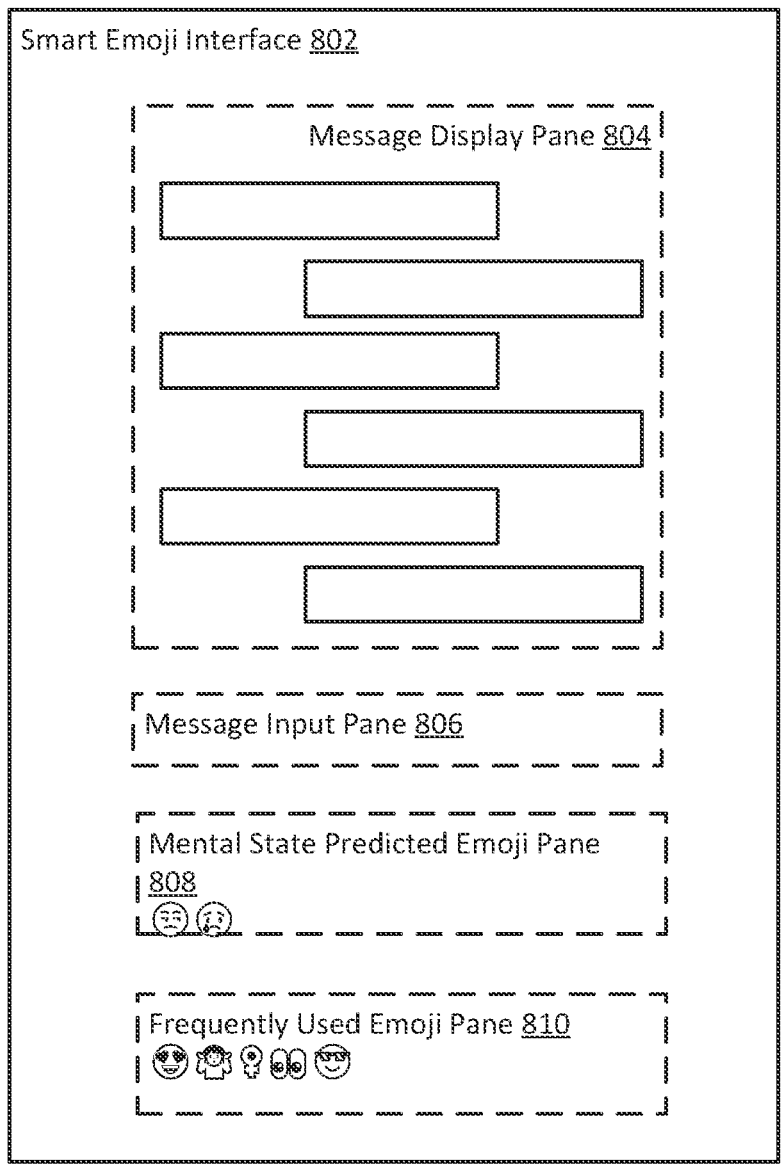
FIG. 8 depicts an example graphical user interface with graphical elements selected and arranged using machine learning-based state prediction according to some embodiments.

FIG. 8 depicts an example graphical user interface (or, smart emoji interface) 802 with graphical elements selected and arranged using machine learning-based state prediction according to some embodiments. In the example of FIG. 8, the graphical user interface 802 includes a message display pane 804, a message input pane 806, a mental state predicted emoji pane 808, and a frequently used emoji pane 810.

In some embodiments, the graphical user interface 802 is an example of the type of interface that may be generated, or at least partially generated, by a machine learning-based state prediction and visualization system 102. For example, the machine learning-based state prediction and visualization system 102 may predict a mental state of a user associated with a user system 104 which presents the graphical user interface 802. In this example, the user is predicted to have a mental state that is associated with an angry emoji and a sad emoji. Accordingly, the angry emoji and the sad emoji are presented in the mental state predicted emoji pane 808. Notably, these are different emojis than the frequently used emojis presented in the frequently used emoji pane 810.

It will be appreciated that the graphical user interface 802 is presented merely by way of example, and that other interfaces generated, or partially generated, by the machine learning-based state prediction and visualization system 102 may different. For example, other interfaces may have elements 804-810 arranged differently, some elements may be removed (e.g., the frequently used emoji pane 810), other elements may be added (e.g., a scrollable list of all available emojis), some elements may be combined (e.g., panes 808 and 810), and/or the like.

Figure 9:
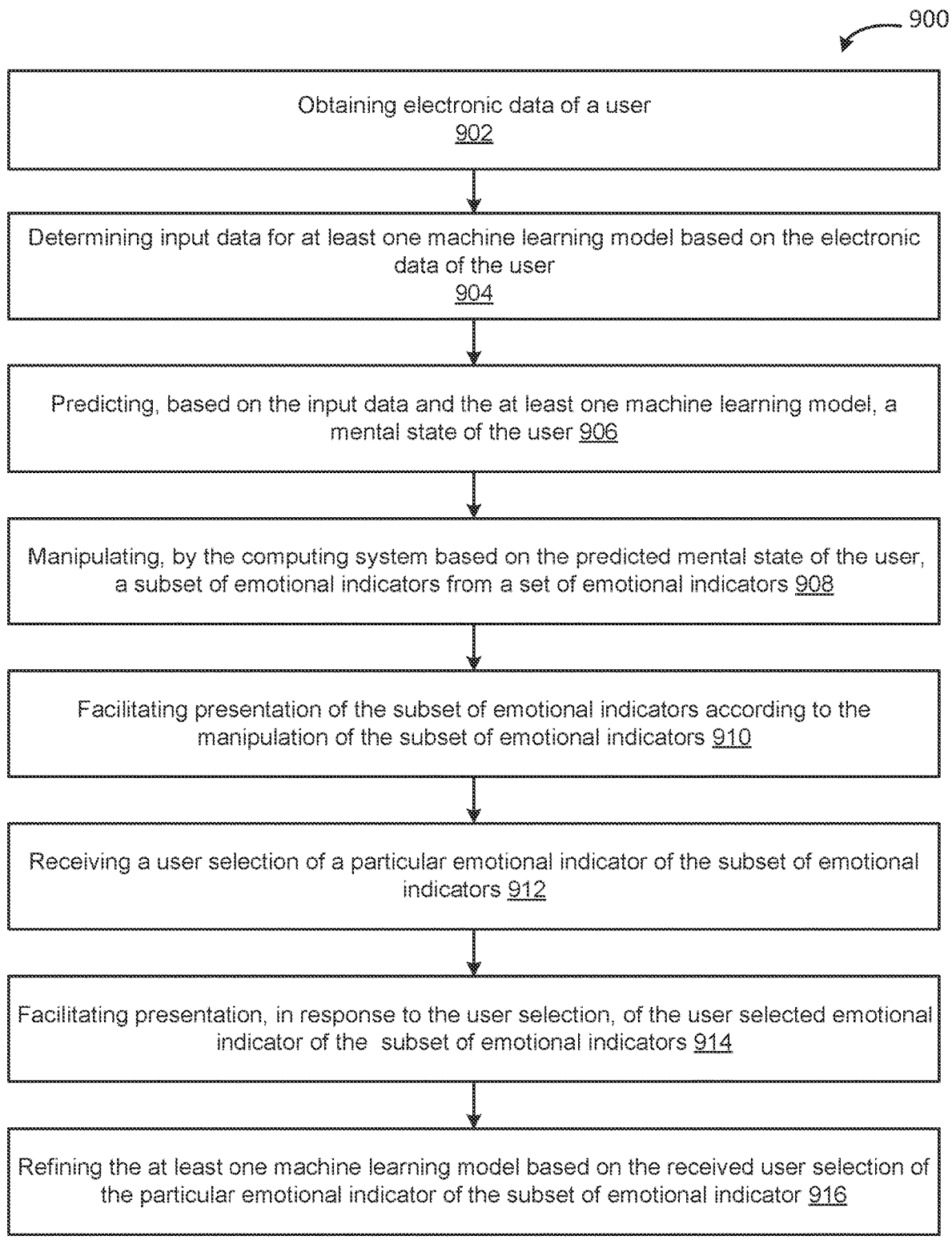
FIG. 9 depicts a flowchart of an example of a method of predicting mental state of a user using machine learning and manipulating (e.g., selecting and arranging) graphical elements based on the user's predicted mental state according to some embodiments.

FIG. 9 depicts a flowchart of an example of a method 900 of predicting mental state of a user using machine learning and manipulating (e.g., selecting and arranging) emotional indicators based on the user's predicted mental state according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 902, a machine learning-based state prediction and visualization system (e.g., machine learning-based state prediction and visualization system 102) obtains electronic data (e.g., electronic data 252) of a user (e.g., user system 104 and/or a user of a user system 104). In some embodiments, a communication engine (e.g., communication engine 220) and/or an electronic data collection engine (e.g., electronic data collection engine 208) obtains the electronic data over a communication network (e.g., communication network 108) from one or more user systems (e.g., user systems 104) and/or one or more third-party systems (e.g., third-party systems 106). A management engine (e.g., management engine 202) may store the electronic data in a datastore (e.g., machine learning-based state prediction and visualization system datastore 240).

In step 904, the machine learning-based state prediction and visualization system determines input data (e.g., machine learning input data 254) for at least one machine learning model (e.g., at least one machine learning model 256) based on the electronic data of the user. In some embodiments, a machine learning input data engine (e.g., machine learning input data engine 210) determines the input data.

In step 906, the machine learning-based state prediction and visualization system predicts, based on the input data and the at least one machine learning model, a mental state of the user. The mental state may comprise a set of mood values (e.g., mood values 260), a set of uncertainty values, and a set of a magnitude values. Each mood value of the set of mood values may be associated with a corresponding uncertainty value of the set of uncertainty values and a corresponding magnitude value of the set of magnitude values. The magnitude value may indicate a relative strength and/or weakness of the associated mood value. In some embodiments, a machine learning-based state prediction engine (e.g., machine learning-based state prediction engine 212) performs the prediction. In some embodiments, the predicted mental state of the user (e.g., at a particular point of time and/or a particular period of time) may be stored by the management engine in a user profile (e.g., a user profile 250) and/or the datastore.

In step 908, the machine learning-based state prediction and visualization system manipulates (e.g., selects and/or arranges), based on the predicted mental state of the user, a subset of emotional indicators (e.g., graphical elements 258) from a set of emotional indicators. For example, the emotional indicators may be graphical elements (e.g., emojis), audio elements, haptic elements, and/or the like. Each emotional indicator of the set of emotional indicators may be associated (e.g., linked) with a corresponding mood value of the set of mood values. Each emotional indicator of the subset of emotional indicators may be associated with the predicted mental state of the user. In some embodiments, a visualization engine (e.g., visualization engine 214) manipulates the emotional indicators based on the mental state of the user (e.g., at one or more points of time and/or one or more periods of time).

In step 910, the machine learning-based state prediction and visualization system facilitates presentation (e.g., display), via a graphical user interface (GUI), of the subset of emotional indicators according to the manipulation of the subset of emotional indicators. For example, the machine learning-based state prediction and visualization system may cause an associated device (e.g., a user system 104 of the user) to present (e.g., display) the subset of emotional indicators according to the manipulation of the subset of emotional indicators. In some embodiments, a presentation engine (e.g., presentation engine 218) and/or the visualization engine facilitates the presentation of the manipulation of the emotional indicators.

In step 912, the machine learning-based state prediction and visualization system receives, in response to the user interacting with the GUI presenting the subset of emotional indicator according to the manipulation of the subset of emotional indicator, a user selection of a particular emotional indicator of the subset of emotional indicator. For example, a user may select a particular emotional indicator presented on their user system, and the selection may be communicated from the user system over the communication network to the communication engine, and the communication engine may then route the received selection to the presentation engine and/or the visualization engine. In some embodiments, the received selection may be used by a feedback engine (e.g., for example, 216) to refine, train, and/or otherwise improve the machine learning model and/ or the machine learning-based state prediction engine.

In step 914, the machine learning-based state prediction and visualization system facilitates presentation (e.g., display), in response to the user selection (e.g., via the GUI), of the user selection of the particular emotional indicator of the subset of emotional indicators. In some embodiments, the presentation engine and/or visualization engine facilitates the presentation of the user selected emotional indicator.

In step 916, the machine learning-based state prediction and visualization system refines the at least one machine learning model based on the received user selection. In some embodiments, a feedback engine (e.g., feedback engine 216) refines the at least one machine learning model.

In some embodiments, step 912, like any of the other steps, may be optional. For example, step 914 may facilitate presentation of the particular emotional indicator in response to a user selection received at the user system (e.g., without the machine learning-based state prediction and visualization system receiving the user selection).

Figure 10:
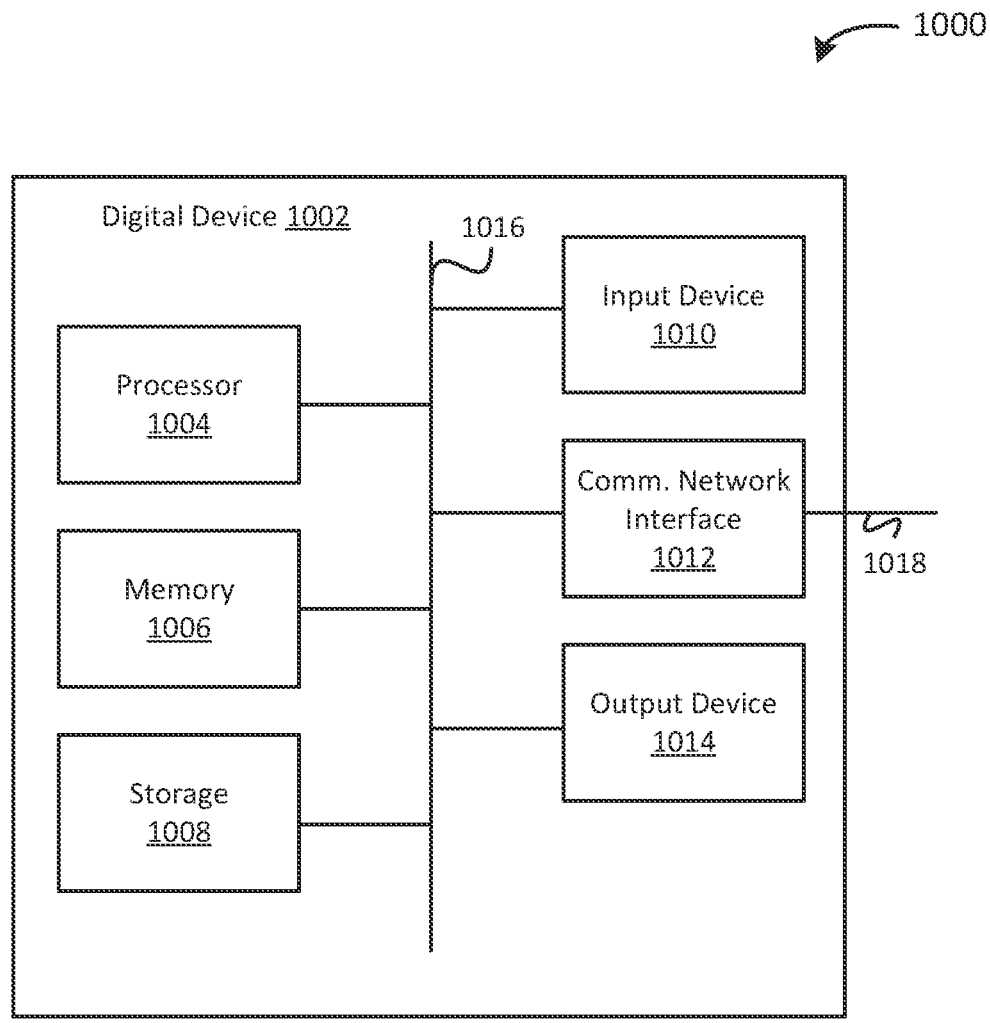
FIG. 10 is a diagram of an example computer system for implementing the features disclosed herein according to some embodiments.

FIG. 10 depicts a diagram 1000 of an example of a computing device 1002. Any of the systems, engines, datastores, and/or networks described herein may comprise an instance of one or more computing devices 1002. In some embodiments, functionality of the computing device 1002 is improved to the perform some or all of the functionality described herein. The computing device 1002 comprises a processor 1004, memory 1006, storage 1008, an input device 1010, a communication network interface 1012, and an output device 1014 communicatively coupled to a communication channel 1016. The processor 1004 is configured to execute executable instructions (e.g., programs). In some embodiments, the processor 1004 comprises circuitry or any processor capable of processing the executable instructions.

The memory 1006 stores data. Some examples of memory 1006 include storage devices, such as RAM, ROM, RAM cache, virtual memory, etc. In various embodiments, working data is stored within the memory 1006. The data within the memory 1006 may be cleared or ultimately transferred to the storage 1008.

The storage 1008 includes any storage configured to retrieve and store data. Some examples of the storage 1008 include flash drives, hard drives, optical drives, cloud storage, and/or magnetic tape. Each of the memory system 1006 and the storage system 1008 comprises a computer-readable medium, which stores instructions or programs executable by processor 1004.

The input device 1010 is any device that inputs data (e.g., mouse and keyboard). The output device 1014 outputs data (e.g., a speaker or display). It will be appreciated that the storage 1008, input device 1010, and output device 1014 may be optional. For example, the routers/switchers may comprise the processor 1004 and memory 1006 as well as a device to receive and output data (e.g., the communication network interface 1012 and/or the output device 1014).

The communication network interface 1012 may be coupled to a network (e.g., network 108) via the link 1018. The communication network interface 1012 may support communication over an Ethernet connection, a serial connection, a parallel connection, and/or an ATA connection. The communication network interface 1012 may also support wireless communication (e.g., 802.11 a/b/g/n, WiMax, LTE, WiFi). It will be apparent that the communication network interface 1012 may support many wired and wireless standards.

It will be appreciated that the hardware elements of the computing device 1002 are not limited to those depicted in FIG. 10. A computing device 1002 may comprise more or less hardware, software and/or firmware components than those depicted (e.g., drivers, operating systems, touch screens, biometric analyzers, and/or the like). Further, hardware elements may share functionality and still be within various embodiments described herein. In one example, encoding and/or decoding may be performed by the processor 1004 and/or a co-processor located on a GPU (i.e., NVidia).

It will be appreciated that an "engine," "system," "datastore," and/or "database" may comprise software, hardware, firmware, and/or circuitry. In one example, one or more software programs comprising instructions capable of being executable by a processor may perform one or more of the functions of the engines, datastores, databases, or systems described herein. In another example, circuitry may perform the same or similar functions. Alternative embodiments may comprise more, less, or functionally equivalent engines, systems, datastores, or databases, and still be within the scope of present embodiments. For example, the functionality of the various systems, engines, datastores, and/or databases may be combined or divided differently. The datastore or database may include cloud storage. It will further be appreciated that the term "or," as used herein, may be construed in either an inclusive or exclusive sense. Moreover, plural instances may be provided for resources, operations, or structures described herein as a single instance.

The datastores described herein may be any suitable structure (e.g., an active database, a relational database, a self-referential database, a table, a matrix, an array, a flat file, a documented-oriented storage system, a non-relational NoSQL system, and the like), and may be cloud-based or otherwise.

The systems, methods, engines, datastores, and/or databases described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented engines may be located in a single geographic location (e.g., within a home environment, an office environment, or a server farm). In other example embodiments, the processors or processor-implemented engines may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

The present invention(s) are described above with reference to example embodiments. It will be apparent to those skilled in the art that various modifications may be made and other embodiments may be used without departing from the broader scope of the present invention(s). Therefore, these and other variations upon the example embodiments are intended to be covered by the present invention(s).

What is claimed is:

1. A computing system comprising:
one or more processors; and
memory storing instructions that, when executed by the one or more processors, cause the computing system to perform:
obtaining electronic data of a user;
determining input data for at least one machine learning model based on the electronic data of the user;
predicting, based on the input data and the at least one machine learning model, a mental state of the user, the mental state comprising a set of mood values, a set of uncertainty values, and a set of a magnitude values, each mood value of the set of mood values being associated with a corresponding uncertainty value of the set of uncertainty values and a corresponding magnitude value of the set of magnitude values, the corresponding magnitude value indicating a relative strength or weakness of the mood value associated with the corresponding uncertainty value and the corresponding magnitude value, wherein the predicting, based on the input data and the at least one machine learning model, the mental state of the user further causes the computing system to perform:
mapping the set of mood values, the set of uncertainty values, and the set of magnitude values to a coordinate system, the coordinate system comprising a plurality of different mood regions, wherein each of the set of mood values is mapped to the coordinate system as a corresponding user point in the coordinate system, and wherein each of the corresponding uncertainty values is mapped as a corresponding radius originating at the corresponding point in the coordinate system;
identifying at least a first mood region of the plurality of different mood regions that includes at least one corresponding user mapped therein;
identifying at least a second mood region of the plurality of different mood regions that does not include any corresponding user points mapped therein, and includes at least a portion of a first radius of the corresponding radii mapped in the coordinate system; and
wherein the mental state of the user is predicted based on the identified at least a first mood region of the plurality of different moods regions, the identified at least a second mood region of the plurality of different mood regions, and the magnitude values associated with the at least one corresponding user point mapped in the at least a first mood region of the plurality of different moods regions and the first radius of the corresponding radii mapped in the coordinate system;

selecting and arranging, by the computing system based on the predicted mental state of the user, a subset of graphical elements from a set of graphical elements, each graphical element of the set of graphical elements being associated with a corresponding mood value of the set of mood values, and each graphical element of the subset of graphical elements being associated with the predicted mental state of the user;

facilitating presentation, via a graphical user interface (GUI), of the subset of graphical elements according to the selection and arrangement of the subset of graphical elements;

receiving, in response to the user interacting with the GUI presenting the subset of graphical elements according to the selection and arrangement of the subset of graphical elements, a user selection of a particular graphical element of the subset of graphical elements; and facilitating presentation, via the GUI in response to the user selection, of the user selected graphical element of the subset of graphical elements.

2. The system of claim 1, wherein each mood value of the set of mood values is associated with a corresponding point in time.

3. The system of claim 1, wherein the set of mood values comprise an angry mood value, a sad mood value, and a happy mood value.

4. The system of claim 1, wherein the electronic data includes text messages sent by the user, email messages sent by the user, voice data of the user, image data of the user, and one or more physical orientations of a device of the user.

5. The system of claim 1, wherein the coordinate system comprises a two-dimensional coordinate system.

6. The system of claim 1, wherein the coordinate system comprises a three-dimensional coordinate system.

7. The system of claim 1, wherein each mood value of the set of mood values is associated with a corresponding point in time.

8. The system of claim 1, wherein the set of graphical elements comprises a set of emojis.

9. A method being implemented by a computing system including one or more physical processors and storage media storing machine-readable instructions, the method comprising:

obtaining electronic data of a user;

determining input data for at least one machine learning model based on the electronic data of the user;

predicting, based on the input data and the at least one machine learning model, a mental state of the user, the mental state comprising a set of mood values, a set of uncertainty values, and a set of a magnitude values, each mood value of the set of mood values being associated with a corresponding uncertainty value of the set of uncertainty values and a corresponding magnitude value of the set of magnitude values, the corresponding magnitude value indicating a relative strength or weakness of the mood value associated with the corresponding uncertainty value and the corresponding magnitude value, wherein the predicting, based on the input data and the at least one machine learning model, the mental state further comprises:

mapping the set of mood values, the set of uncertainty values, and the set of magnitude values to a coordinate system, the coordinate system comprising a plurality of different mood regions, wherein each of the set of mood values is mapped to the coordinate system as a corresponding user point in the coordinate system, and wherein each of the corresponding uncertainty values is mapped as a corresponding radius originating at the corresponding point in the coordinate system;

identifying at least a first mood region of the plurality of different mood regions that includes at least one corresponding user mapped therein;

identifying at least a second mood region of the plurality of different mood regions that does not include any corresponding user points mapped therein, and includes at least a portion of a first radius of the corresponding radii mapped in the coordinate system; and wherein the mental state of the user is predicted based on the identified at least a first mood region of the plurality of different moods regions, the identified at least a second mood region of the plurality of different mood regions, and the magnitude values associated with the at least one corresponding user point mapped in the at least a first mood region of the plurality of different moods regions and the first radius of the corresponding radii mapped in the coordinate system;

selecting and arranging, by the computing system based on the predicted mental state of the user, a subset of graphical elements from a set of graphical elements, each graphical element of the set of graphical elements being associated with a corresponding mood value of the set of mood values, and each graphical element of the subset of graphical elements being associated with the predicted mental state of the user;

facilitating presentation, via a graphical user interface (GUI), of the subset of graphical elements according to the selection and arrangement of the subset of graphical elements;

receiving, in response to the user interacting with the GUI presenting the subset of graphical elements according to the selection and arrangement of the subset of graphical elements, a user selection of a particular graphical element of the subset of graphical elements; and facilitating presentation, via the GUI in response to the user selection, of the user selected graphical element of the subset of graphical elements.

10. The method of claim 9, wherein each mood value of the set of mood values is associated with a corresponding point in time.

11. The method of claim 9, wherein the set of mood values comprise an angry mood value, a sad mood value, and a happy mood value.

12. The method of claim 9, wherein the electronic data includes text messages sent by the user, email messages sent by the user, voice data of the user, image data of the user, and one or more physical orientations of a device of the user.

13. The method of claim 9, wherein the coordinate system comprises a two-dimensional coordinate system.

14. The method of claim 9, wherein the coordinate system comprises a three-dimensional coordinate system.

15. The method of claim 9, wherein each mood value of the set of mood values is associated with a corresponding point in time.

16. The method of claim 9, wherein the set of graphical elements comprises a set of emojis.

17. A non-transitory computer readable medium comprising instructions that, when executed, cause one or more processors to perform:

obtaining electronic data of a user;

determining input data for at least one machine learning model based on the electronic data of the user;

predicting, based on the input data and the at least one machine learning model, a mental state of the user, the mental state comprising a set of mood values, a set of uncertainty values, and a set of a magnitude values, each mood value of the set of mood values being associated with a corresponding uncertainty value of the set of uncertainty values and a corresponding magnitude value of the set of magnitude values, the corresponding magnitude value indicating a relative strength or weakness of the mood value associated with the corresponding uncertainty value and the corresponding magnitude value, wherein the predicting, based on the input data and the at least one machine learning model, the mental state further comprises:

mapping the set of mood values, the set of uncertainty values, and the set of magnitude values to a coordinate system, the coordinate system comprising a plurality of different mood regions, wherein each of the set of mood values is mapped to the coordinate system as a corresponding user point in the coordinate system, and wherein each of the corresponding uncertainty values is mapped as a corresponding radius originating at the corresponding point in the coordinate system;

identifying at least a first mood region of the plurality of different mood regions that includes at least one corresponding user mapped therein;

identifying at least a second mood region of the plurality of different mood regions that does not include any corresponding user points mapped therein, and includes at least a portion of a first radius of the corresponding radii mapped in the coordinate system; and wherein the mental state of the user is predicted based on the identified at least a first mood region of the plurality of different moods regions, the identified at least a second mood region of the plurality of different mood regions, and the magnitude values associated with the at least one corresponding user point mapped in the at least a first mood region of the plurality of different moods regions and the first radius of the corresponding radii mapped in the coordinate system;

selecting and arranging, by the computing system based on the predicted mental state of the user, a subset of graphical elements from a set of graphical elements, each graphical element of the set of graphical elements being associated with a corresponding mood value of the set of mood values, and each graphical element of the subset of graphical elements being associated with the predicted mental state of the user;

facilitating presentation, via a graphical user interface (GUI), of the subset of graphical elements according to the selection and arrangement of the subset of graphical elements;

receiving, in response to the user interacting with the GUI presenting the subset of graphical elements according to the selection and arrangement of the subset of graphical elements, a user selection of a particular graphical element of the subset of graphical elements; and facilitating presentation, via the GUI in response to the user selection, of the user selected graphical element of the subset of graphical elements.

* * * * *